US012751940B2

(12) United States Patent
Greene et al.

(10) Patent No.: US 12,751,940 B2
(45) **Date of Patent: *Oct. 6, 2026**

(54) METHODS FOR DELIVERY OF PSYCHEDELIC MEDICATIONS BY INHALATION AND SYSTEMS FOR PERFORMING THE METHODS

(71) Applicant: CYBIN IRL LIMITED, Dublin (IE)

(72) Inventors: Brett J. Greene, Fitchburg, MA (US); Michael Palfreyman, St. Petersburg, FL (US); Alex Nivorozhkin, West Roxbury, MA (US); Robert Mino, Jupiter, FL (US)

(73) Assignee: Cybin IRL Limited, Dublin (IE)

( * ) Notice: Subject to any disclaimer, the term of this patent is extended or adjusted under 35 U.S.C. 154(b) by 551 days.

This patent is subject to a terminal disclaimer.

(21) Appl. No.: 18/027,810

(22) PCT Filed: Oct. 1, 2021

(86) PCT No.: PCT/EP2021/077057

§ 371 (c)(1),
(2) Date: Mar. 22, 2023

(87) PCT Pub. No.: WO2022/069690

PCT Pub. Date: Apr. 7, 2022

(65) Prior Publication Data

US 2023/0355583 A1 Nov. 9, 2023

Related U.S. Application Data

(60) Provisional application No. 63/086,830, filed on Oct. 2, 2020, provisional application No. 63/114,769, filed on Nov. 17, 2020, provisional application No. 63/241,891, filed on Sep. 8, 2021.

(51) Int. Cl.

| | |
|---|---|
| ***A61K 31/4045*** | (2006.01) |
| ***A61K 9/00*** | (2006.01) |
| ***A61K 33/00*** | (2006.01) |
| ***A61M 11/00*** | (2006.01) |
| ***A61M 15/00*** | (2006.01) |
| ***A61M 16/12*** | (2006.01) |

(52) U.S. Cl.

CPC ........ *A61K 31/4045* (2013.01); *A61K 9/0075* (2013.01); *A61K 9/0078* (2013.01); *A61K 9/008* (2013.01); *A61K 33/00* (2013.01); *A61M 11/005* (2013.01); *A61M 15/0021* (2014.02); *A61M 16/12* (2013.01); *A61M 2202/0283* (2013.01)

(58) Field of Classification Search

CPC .............. A61K 31/4045; A61K 9/0075; A61K 9/0078; A61K 9/008; A61K 33/00; A61M 16/12; A61M 15/00

See application file for complete search history.

(56) References Cited

U.S. PATENT DOCUMENTS

| | | | | |
|---|---|---|---|---|
| 6,232,475 B1 | | 5/2001 | Mueller et al. | |
| 11,242,318 B2 | * | 2/2022 | Nivorozhkin | A61P 25/00 |
| 11,246,860 B2 | | 2/2022 | Kristensen et al. | |
| 11,633,390 B2 | | 4/2023 | Kristensen et al. | |
| 11,642,336 B2 | | 5/2023 | Kristensen et al. | |
| 11,746,088 B2 | * | 9/2023 | Nivorozhkin | A61K 9/20 514/415 |
| 11,834,410 B2 | * | 12/2023 | Nivorozhkin | C07F 9/572 |
| 12,240,813 B2 | * | 3/2025 | Nivorozhkin | C07F 9/572 |
| 12,630,504 B2 | | 5/2026 | Belser et al. | |
| 2004/0127574 A1 | | 7/2004 | Kori et al. | |
| 2008/0241255 A1 | | 10/2008 | Rose et al. | |
| 2009/0318454 A1 | * | 12/2009 | Weiner | C07D 261/20 514/567 |
| 2017/0320831 A1 | * | 11/2017 | Xiong | A61P 25/04 |
| 2020/0261379 A1 | | 8/2020 | Mcgowan et al. | |
| 2021/0015833 A1 | | 1/2021 | Larosa et al. | |
| 2022/0267252 A1 | | 8/2022 | Traschel et al. | |
| 2022/0323378 A1 | | 10/2022 | Joseph | |
| 2023/0312464 A1 | | 10/2023 | Belser et al. | |

(Continued)

FOREIGN PATENT DOCUMENTS

| | | |
|---|---|---|
| CA | 3007870 C | 3/2024 |
| CN | 112430187 A | 3/2021 |

(Continued)

OTHER PUBLICATIONS

Goode et al (Improvement in aerosol delivery with helium-oxygen mixtures during mechanical ventilation), Am J Respir Crit Care Med vol. 163. pp. 109-114. (Year: 2001).*

AZ04784681(ON) Database accession No. 2022733918, “2-(5-methoxy-2H-1,3-benzoxathiol-6-yl)ethan-1-amine”, STN01 Mar. 2019, CHEMCATS.

AZ04786463 Database accession No. 0915409267, “[2-(5-methoxy)-2H-1,3-benzoxythiol-6-yl)ethyl](methyl)amine”, STN01 Mar. 2019, CHEMCATS.

AZ05479357(ON)Database accession No. 1334856705, Azepine H C, “2-(5-methoxy-2H-1,3-benzoxathiol-6-yl)propan-1-amine”, STN01 Mar. 2019 (Mar. 1, 2019), CHEMCATS.

AZ05508757 Database accession No. 0103296540, Azepine O M, “1-(5-methoxy-2H-1,3-benzoxathiol-6-yl)-2-methylpropan-2-amine”, STN01 Mar. 2019, CHEMCATS.

(Continued)

*Primary Examiner* — Mina Haghighatian

(74) *Attorney, Agent, or Firm* — Lathrop GPM LLP; Lisa Hillman

(57) ABSTRACT

Provided are methods for delivering psychedelic drugs to a patient in need thereof comprising administering via inhalation of a psychedelic drug in the form of an aerosol, methods for treating a central nervous system (CNS) disorder or psychological disorder via inhalation of a psychedelic drug in the form of an aerosol, devices for delivery of psychedelic drug and nitrous oxide mixtures by inhalation, including with remote activation and control, and methods for treating a central nervous system (CNS) disorder or psychological disorder via inhalation of nitrous oxide/oxygen mixtures having an amount of nitrous oxide of 15 to 25% by volume of total gas.

20 Claims, No Drawings

(56) References Cited

U.S. PATENT DOCUMENTS

| | | | |
|---|---|---|---|
| 2024/0425451 | A1 | 12/2024 | Belser et al. |
| 2025/0145566 | A1 | 5/2025 | Nivorozhkin et al. |
| 2025/0205198 | A1 | 6/2025 | Palfreyman et al. |
| 2025/0236589 | A1 | 7/2025 | Nivorozhkin et al. |

FOREIGN PATENT DOCUMENTS

| | | | |
|---|---|---|---|
| JP | 2000-198767 | A | 7/2000 |
| JP | 2002-293764 | A | 10/2002 |
| JP | 2008-516974 | A | 5/2008 |
| JP | 2020-520358 | A | 7/2020 |
| WO | WO 2006/044732 | A2 | 4/2006 |
| WO | WO 2006/079999 | A2 | 8/2006 |
| WO | WO 2008/016677 | A2 | 2/2008 |
| WO | WO 2008/016677 | A3 | 2/2008 |
| WO | WO 2008/121610 | A1 | 10/2008 |
| WO | WO 2010/019467 | A1 | 2/2010 |
| WO | WO 2016/040822 | A1 | 3/2016 |
| WO | WO 2018/210988 | A1 | 11/2018 |
| WO | WO 2019/081764 | A1 | 5/2019 |
| WO | WO 2019/099745 | A1 | 5/2019 |
| WO | WO 2020/041329 | A1 | 2/2020 |
| WO | WO 2020/169850 | A1 | 8/2020 |
| WO | WO 2020/169851 | A1 | 8/2020 |
| WO | WO 2020/181194 | A1 | 9/2020 |
| WO | WO 2020/212951 | A1 | 10/2020 |
| WO | WO 2020/245133 | A1 | 12/2020 |
| WO | WO 2021/003467 | A1 | 1/2021 |
| WO | WO 2021/116503 | A2 | 6/2021 |
| WO | WO 2021/116503 | A8 | 6/2021 |
| WO | WO 2021/234608 | A1 | 11/2021 |
| WO | WO 2022/038170 | A1 | 2/2022 |
| WO | WO 2022/038171 | A1 | 2/2022 |
| WO | WO 2022/069690 | A2 | 4/2022 |
| WO | WO 2022/069690 | A3 | 4/2022 |
| WO | WO 2022/182602 | A2 | 9/2022 |
| WO | WO 2022/195489 | A2 | 9/2022 |
| WO | WO 2022/221942 | A1 | 10/2022 |
| WO | WO 2022/225884 | A1 | 10/2022 |
| WO | WO 2022/261240 | A2 | 12/2022 |
| WO | WO 2022/271982 | A1 | 12/2022 |
| WO | WO 2022/261240 | A3 | 1/2023 |
| WO | WO 2023/283386 | A2 | 1/2023 |
| WO | WO 2023/288013 | A2 | 1/2023 |
| WO | WO 2023/023351 | A1 | 2/2023 |
| WO | WO 2023/283386 | A3 | 2/2023 |
| WO | WO 2023/036473 | A1 | 3/2023 |
| WO | WO 2023/049480 | A1 | 3/2023 |

OTHER PUBLICATIONS

AZ06532047 (ON) Database accession No. 0797974793, Alex Kizi, "2-amino-3-(5-methoxy-2H-1,3-benzoxathiol-6-yl)propanenitrile", STN01 Mar. 2019, CHEMCATS.

Beaton et al., "A Comparison of the Behavioral Effects of Proteo- and Deutero-N, N-Dimethyltryptamine", Pharmacology Biochemistry & Behavior, 1982, 16: 811-814.

Bijlsma et al., "Fragmentation pathways of drugs of abuse and their metabolites based on QTOF MS/MS and MSE accurate-mass spectra", Journal of Mass Spectrometry, Sep. 1, 2011, 46(9): 865-875.

Bjornstad et al., "Development and Clinical Application of an LC-MS-MS Method for Mescaline in Urine", Journal of Analytical Toxicology, Apr. 2008, 32(3): 227-231.

Borchardt et al., "General methods for the preparation of [alpha] and/OR [beta] deuterium labelled 6-hydroxydopamine derivatives", Journal of Labelled Compounds and Radiopharmaceuticals, vol. 19, No. 3, Mar. 1, 1982, pp. 433-445.

Database Caplus [online] Dec. 29, 2009 (Dec. 29, 2009), Chen: "A series of deuterium labelled phenylalkylamines as drug testing standards", XP055867027, Database accession No. 2010:371880.

Database Registry [online] Oct. 22, 2009 (Oct. 22, 2009), Chemcats N: "2-[4-methyl-2,5- bis(trideuteriomethoxy)phenyl]ethanamine", XP055866937, Database accession No. 1189574-92-2.

Database Registry [online] Chemical Abstracts Service, Columbus, Ohio, US; Oct. 22, 2009 (Oct. 22, 2009), "2,5-(Dimethoxy-d6)-4-methylphenethylamine Hydrochloride", XP055866918, accession No. 1725444279 (CHEMCATS) Database accession No. 1189467-51-3.

Database Registry [online] Chemical Abstracts Service, Columbus, Ohio, US; Oct. 25, 2009 (Oct. 25, 2009), "2C-B-d6 Hydrochloride", XP055866926, accession No. 2145931586 (CHEMCATS) Database accession No. 1189978-45-7.

Database Registry [online] Chemical Abstracts Service, Columbus, Ohio, US; Oct. 26, 2007 (Oct. 26, 2007), "Benzeneethanamine, 4-chloro-2,5-di(methoxy-d3)-", XP055866907, accession No. 1144584103 (CHEMCATS) Database accession No. 951442-78-7.

Database Registry [online] Chemical Abstracts Service, Columbus, Ohio, US; Apr. 5, 2010 (Apr. 5, 2010), "2,5-(Dimethoxy-d6)-4-iodophenethylamine Hydrochloride", XP055866911, accession No. 1819317403 (CHEMCATS) Database accession No. 1216685-82-3.

Duman et al., "Signaling pathways underlying the rapid antidepressant actions of ketamine", Neuropharmacology, 2012, 62: 35-41.

Duman et al., "Synaptic dysfunction in depression: potential therapeutic targets," Science, 2012, 338: 68-72.

Dwyer et al., "mTOR activation is required for the antidepressant effects of mGluR(2)/(3) blockade", Int. J. Neuropsychoph, 2012, 15: 429-434.

Gardenhire et al., "A Guide to Aerosol Delivery Devices for Respiratory Therapists" 4th Edition, Jan. 1, 2017.

Gillman, "Mini-Review: A Brief History of Nitrous Oxide (N2O) Use in Neuropsychiatry", Current Drug Abuse Reviews, Jun. 2019, 11(1): 12-20.

Gupta et al., "Heliox administration in the pediatric intensive care unit: An evidence-based review", Pediatr Crit Care Med., Mar. 1, 2005, 6(2): 204-211.

Hamishehkar et al., "The Role of Carrier in Dry Powder Inhaler", Recent Advances in Novel Drug Carrier Systems, Oct. 31, 2012, InTech.

Hanan et al., "Pharmacy Practice for Technicians", Fifth Edition, Jan. 3, 2014, p. 261.

Heuer et al., "Comprehensive Respiratory Therapy Exam Preparation Guide", Chapter 12: Administer Medication and Speciality Gases (Section III-D), p. 293, Feb. 22, 2020.

Iida et al., "Preparation of dry powder inhalation by surface treatment of lactose carrier particles." Chem Pharm Bull, 2003, 511150009-2363.

International Search Report and Written Opinion for PCT International Patent Application No. PCT/EP2021/072896, mailed Feb. 4, 2022.

International Search Report and Written Opinion for PCT International Patent Application No. PCT/EP2021/072898, mailed Feb. 4, 2022.

International Search Report and Written Opinion for PCT International Patent Application No. PCT/EP2021/077057, mailed Mar. 18, 2022.

International Search Report and Written Opinion for PCT International Patent Application No. PCT/EP2022/058574, mailed Sep. 12, 2022.

International Search Report and Written Opinion for PCT International Patent Application No. PCT/EP2023/053744, mailed May 19, 2023.

International Search Report and Written Opinion for PCT International Patent Application No. PCT/EP2023/053752, mailed May 11, 2023.

International Search Report and Written Opinion for PCT International Patent Application No. PCT/EP2023/057939, mailed Aug. 14, 2023.

International Search Report and Written Opinion for PCT International Patent Application No. PCT/EP2023/058107, mailed Jul. 23, 2023.

Jernigan et al., "The mTOR signaling pathway in the prefrontal cortex is compromised in major depressive disorde", Prog neuropsychoph, 2011, 35: 1774-1779.

Li et al., "mTOR-dependent synapse formation underlies the rapid antidepressant effects of NMDA antagonists", Science, 2010, 329: 959-964.

(56) References Cited

OTHER PUBLICATIONS

Ly et al., "Psychedelics Promote Structural and Functional Neural Plasticity", Cell Rep., 2018, 23(11): 3170-3182.
Mckenna et al., "3,4-Methylenedioxyamphetamine (MDA) analogues exhibit differential effects on synaptosomal release of Ô3H-dopamine and Ô3H-5-hydroxytryptamine", Mar. 1, 1991, 38(3): 505-512.
Monte et al., "Dihydrobenzofuran analogues of hallucinogens. 3. Models of 4-substituted (2,5-dimethoxyphenyl)alkylamine derivatives with rigidified methoxy groups", J Med Chem., Jul. 1996, vol. 39, No. 15, pp. 2953-2961.
Monte et al., "Dihydrobenzofuran analogues of hallucinogens. 4. Mescaline derivatives", Sep. 12, 1997, vol. 40, No. 19, pp. 2997-3008.
Nagele et al., "Nitrous Oxide for Treatment-Resistant Major Depression: A Proof-of-Concept Trial", Biol Psychiatry, Jul. 2015, 78(1): 10-18.
Nagele et al., "A phase 2 trial of inhaled nitrous oxide for treatment-resistant major depression", *Science Transl. Med.*, Jun. 9, 2021, 13(597): eabe1376.
Nichols et al., "1-(2,5-Dimethoxy-4-(trifluoromethyl)phenyl)-2-aminopropane: A Potent Serotonin 5-HT2A/2C Agonist", Journal of Medicinal Chemistry, vol. 37, No. 25, Dec. 1, 1994, pp. 4346-4351.
Partial International Search Report and Invitation to Pay Additional Fees and, Where Applicable, Protest Fee for PCT International Patent Applciation No. PCT/EP2023/057939, mailed Jun. 16, 2023.
Pham et al., "Ketamine treatment involves medial prefrontal cortex serotonin to induce a rapid antidepressant-like activity in BALB/cJ mice", Neuropharmacology, Jan. 2017, 112(Pt A): 198-209, Epublished May 17, 2016.
Psychonautwiki, 2C-T-x, Retrieved from internet Apr. 21, 2023.
Sepeda et al., "Inhaled 5-methoxy-N,N-dimethyltryptamine: Supportive context associated with positive acute and enduring effects", Journal of Psychadelic Studies, Jun. 1, 2020, 4(2): 114-122.
Sial et al., "Ketamine: The final frontier or another depressing end?", Behav Brain Res., 2020, 383: 112508.
Simmons et al., "Regioselective syntheses of deuterium labelled 6-hydroxydopamines", Journal of Labelled Compounds and Radiopharmaceuticals, vol. 20, No. 3, Mar. 1, 1983, pp. 325-338.
Simoes et al., "Dried blood spots combined to an UPLC-MS/MS method for the simultaneous determination of drugs of abuse in forensic toxicology", Journal Of Pharmaceutical And Biomedical Analysis, Jan. 1, 2018, 147: 634-644.
Tang et al., "Involvement of normalized NMDA receptor and mTOR-related signaling in rapid antidepressant effects of Yueju and ketamine on chronically stressed mice", Sci Rep 5, 2015, 13573.
Traschel et al., "Flourine in psychadelic phenethylamines", Drug Testing and Analysis, Feb. 28, 2012, 4: 577-590.
Trachsel et al., "Synthesis of Fluoro Analogues of 3,4-(Methylenedioxy)amphetamine (MDA) and Its Derivatives", Chemistry & Biodiversity, Mar. 1, 2006, 3(3): 326-336.
Traschel, "Synthesis of Novel (Phenylalkyl)amines for the Investigation of Structure ± Activity Relationships", Helvetica Chimica Acta, 2003, 86: 2610-2619.
Wikipedia, 2C (psychedelics), Retrieved from internet Apr. 21, 2023.
Wikipedia, Substituted phenethylamine, Retrieved from internet Apr. 21, 2023.
Blaazer et al., "Structure—Activity Relationships of Phenylalkylamines as Agonist Ligands for 5-HT2A Receptors," ChemMedChem, Jan. 15, 2008, 3(9): 1299-1309.
Heresco-Levy et al., "Synergistic psychedelic—NMDAR modulator treatment forneuropsychiatric disorders", Molecular Psychiatry, Nov. 9, 2023.
International Search Report and Written Opinion for PCT International Patent Application No. PCT/EP2023/080027, mailed Feb. 8, 2024.
Kanamori et al., "A model system for prediction of the in vivo metabolism of designer drugs using three-dimensional culture of rat and human hepatocytes", Forensic Toxicology, Jun. 4, 2011, 29(2): 142-151.
Kanamori et al., "In vivo metabolism of 2, 5-dimethoxy-4-propylthiophenethylamine in rat", Xenobiotica, Jun. 2007, 37(6): 679-692.
Krempien et al., "Randomized, Double-Blind, Placebo-Controlled Study to Evaluate the Safety and Efficacy of CYB003, a Deuterated Psilocybin Analog in Patients with Major Depressive Disorder", ACNP 2023.
Li et al., "Effects of Direct- and Indirect-Acting Serotonin Receptor Agonists on the Antinociceptive and Discriminative Stimulus Effects of Morphine in Phesus Monkeys", Neuropsychology, 2011, 36: 940-949.
Patani et al., "Bioisosterism: A Rational Approach in Drug Design," Chem. Rev., 1996, 96(8): 3147-3176.
Shah et al., "The role of fluorine in medicinal chemistry," Journal of Enzyme Inhibition and Medicinal Chemistry, 2007, 22(5): 527-540.
Stella et al., "Prodrugs: Some Thoughts and Current Issues," J. Pharmaceutical Sciences, 2010, 99(12): 4755-4765.
Yale et al., "The Trifluoromethyl Group in Medical Chemistry," Journal of Medicinal and Pharmaceutical Chemistry, 1959, 1(2): 121-133.
U.S. Appl. No. 18/730,423, filed Jul. 19, 2024, Alex Nivorozhkin, Phenethylamine Derivatives, Compositions, and Methods of Use.
U.S. Appl. No. 18/688,125 2024/0366655, filed Mar. 31, 2022 Nov. 7, 2024, Michael Palfreyman, Combination Drug Therapies.
U.S. Appl. No. 18/852,115, filed Sep. 27, 2024, Michael Palfreyman, Combination Drug Therapies.
U.S. Appl. No. 18/825,122, filed Sep. 5, 2024, Alex Belser, Therapeutic Phenethylamine Compositions and Methods of Use.
U.S. Appl. No. 18/850,356, filed Sep. 24, 2024, Brett J. Greene, Methods for Delivery of Psychedelic Medications by Inhalation and Systems for Performing the Methods.
U.S. Appl. No. 18/730,397, filed Jul. 19, 2024, Alex Nivorozhkin, Therapeutic Phenethylamine Compositions and Methods of Use.
Barker et al., "Comparison of the brain levels of N,N-dimethyltryptamine and alpha, alpha, beta, beta-tetradeutero-N-N-dimethyltryptamine following intraperitoneal injection. The in vivo kinetic isotope effect", Biochem Pharmacol., Aug. 1, 1982, 31(15): 2513-2516.
Buttini et al., "The application of Quality by Design framework in the pharmaceutical development of dry powder inhalers", Eur. J. Pharm. Sci., Feb. 15, 2018, 113: 64-76. Epub Nov. 23, 2017.
Cheze et al., "Simultaneous analysis of six amphetamines and analogues in hair, blood and urine by LC-ESI-MS/MS", Forensic Science International, Jul. 26, 2007, 170(2-3): 100-104.
Ding et al., "Rapid, regiospecific syntheses of deuterium substituted 6-[18F]fluorodopamine (α,α-D2; β,β-D2 and α,α,β,β-D4) for mechanistic studies with positron emission tomography", Journal of Labelled Compounds and Radiopharmaceuticals, Jul. 1993, 33(7): 645-654.
Ding et al., "Reductive Deuteration of Nitriles Using D2O as a Deuterium Source", Journal of Organic Chemistry, Oct. 14, 2019, 84(23): 15098-15105.
Foster et al., "Deuterium isotope effects in studies of drug metabolism", Trends in Pharmacological Sciences, 1985, 5: 524-527.
Goode et al., "Improvement in aersol delivery with helium-oxygen mixtures during mechanical ventilation", Am. J. Respir. Crit. Care Med., Jan. 2001, 163(1): 109-114.
Hesselgren et al., "Synthesis of six specifically deuterted indoles of biological interest", J. Labelled Compounds and Radiopharmaceuticals, May/Jun. 1980, 17(3): 411-419.
Islam et al., "Developing an efficient and reliable dry powder inhaler for pulmonary drug delivery—a review for multidisciplinary researchers", Med. Eng. Phys., May 2012, 34(4):409-427. Epub Jan. 23, 2012.
Magarvey et al., "Biosynthetic Characterization and Chemoenzymatic Assembly of the Cryptophycins. Potent Anticancer Agents from Nostoc Cyanobionts", ACS Chemical Biology, Dec. 15, 2006, 1(12): 766-779.

(56) References Cited

OTHER PUBLICATIONS

RN 2112331-94-7 and others, Aug. 11, 2017, Database Registry [Online], Retrieved from STN on May 1, 2025.
Shaikh et al., "Synthesis of deuterium-labelled standards of (±)-DOM and (±)-MMDA", Journal of Labelled Compounds and Radiopharmaceuticals, Jun. 4, 2007, 50(7): 660-665.
Tearavarich et al., "Microwave-accelerated preparation and analytical characterization of 5-ethoxy-N,N-dialkyl-[α,α,β,β-H(4) ]- and [α,α,β,β-D(4) ]-tryptamines", Drug Test Anal., Sep. 2011, 3(9): 597-608. Epub Dec. 29, 2010.
Timmins, "Deuterated drugs; where are we now?", Expert Opin. Ther. Pat., Jul. 29, 2014, 24(10): 1067-1075.
Walline et al., "Comparative Molecular Field Analysis Using Selectivity Fields Reveals Residues in the Third Transmembrane Helix of the Serotonin Transporter Associated with Substrate and Antagonist Recognition", The Journal of Pharmacology and Experimental Therapeutics, Jun. 2008, 325(3): 791-800.
Adaviri, "The Event-Informational Singularity—DPT & Ketamine", EROWID Experience Vaults, May 21, 2013, Retrieved from url: https://www.erowid.org/experiences/exp.php?ID=100230.
Aftergas Fog, "An Outrageous Combination—DMT & Nitrous Oxide", EROWID Experience Vaults, Sep. 28, 2007, Retrieved from url: https://www.erowid.org/experiences/exp.php?ID=66034.
Dailey et al., "Aerosol Delivery Through Adult High Flow Nasal Cannula With Heliox and Oxygen", Respir. Care, Sep. 2017, 62(9): 1186-1192.
Indigo, "Traveling thru Headspace and Time—5-MeO-DiPT & Nitrous Oxide", EROWID Experience Vaults, Jun. 18, 2006, Retrieved from url: https://www.erowid.org/experiences/exp.php?ID=22618.
Inner Explorer, "Choosing to Stay in My Body—Ketamine & 5-MeO-DMT", EROWID Experience Vaults, Sep. 29, 2017, Retrieved from url: https://www.erowid.org/experiences/exp.php?ID=110796.
Psychonaut Om Elf, "Visting Friends in Another Universe—DMT & Nitrous Oxide", EROWID Experience Vaults, Jun. 18, 2006, Retrieved from url: https://www.erowid.org/experiences/exp.php?ID=74289.
Third Party Submission dated Jul. 7, 2025, for U.S. Appl. No. 18/730,423, filed Jul. 24, 2024.
Trypit, "Touch-Controlled Universes in Total Darkness—5-MeO-DMT & Nitrous Oxide", EROWID Experience Vaults, Oct. 6, 2005 Retrieved from url: https://www.erowid.org/experiences/exp.php?ID=42203.
Luethi et al., "Monoamine receptor interaction profiles of 4-thio-substituted phenethylamines (2C-T drugs)", Neuropharmacology, May 15, 2018, 134(Pt. A): 141-148, Epublished Jul. 15, 2017.
Database Registry [online] PUBCHEM, 2004, "Benzeneethanamine, 4-chloro- 2,5-di(methoxy-d3)-", PubChem CID: 12063262, Database Registry No. 648957-54- 4.
Bisaga et al., "Therapeutic potential of NMDA receptor antagonists in the treatment of alcohol and substance use disorders", Expert Opinion on Investigational Drugs, Feb. 2005, 9(10): 2233-2248.
Database Registry [online] Chemical Abstracts Service, Columbus, OH, US, May 7, 2026, "α-(Aminomethyl)-5-methoxy-1,3-benzoxathiole-6-acetonitrile", CAS Registry No. 2092852-03-2.
Database Registry [online] Chemical Abstracts Service, Columbus, OH, US, May 7, 2026, "α-Amino-5-methoxy-1,3-benzoxathiole-6-propanenitrile", CAS Registry No. 2092561-88-9.
Database Registry [online] Chemical Abstracts Service, Columbus, OH, US, May 7, 2026, "5-Methoxy-α,α-dimethyl-1,3-benzoxathiole-6-ethanamine", CAS Registry No. 1898377-53-1.
Database Registry [online] Chemical Abstracts Service, Columbus, OH, US, May 7, 2026, "5-Methoxy-β-methyl-1,3-benzoxathiole-6-ethanamine", CAS Registry No. 1891826-14-4.
Database Registry [online] Chemical Abstracts Service, Columbus, OH, US, May 7, 2026, "5-Methoxy-N-methyl-1,3-benzoxathiole-6-ethanamine", CAS Registry No. 1780063-36-6.
Database Registry [online] Chemical Abstracts Service, Columbus, Oh, US, May 7, 2026, "5-Methoxy-1,3-benzoxathiole-6-ethanamine", CAS Registry No. 1554460-43-3.
European Examination Report for EP Patent Application No. 22716971.1, dated May 27, 2026.
Geddes, "Psychedelic drug DMT to be trialled in UK to treat depression", a newspaper article from The Guardian published on Dec. 9, 2020, Retrieved fron url: <https://www.theguardian.com/science/2020/dec/09/psychedelic-drug-dmt-to-be-trialled-in-uk-to-treat-depression>.
Gouzoulis-Mayfrank et al., "Psychological Effects of (S)-Ketamine and N,N-Dimethyltryptamine (DMT): A Double-Blind, Cross-Over Study in Healthy Volunteers", Pharmacopsychiatry, 2005, 38(6): 301-311.
Nagele et al., "Exploring Nitrous Oxide as Treatment for Mood Disorders: Basic Concepts", J Clin Psychopharmacol., Apr. 2018, 38(2): 144-148.

* cited by examiner

METHODS FOR DELIVERY OF PSYCHEDELIC MEDICATIONS BY INHALATION AND SYSTEMS FOR PERFORMING THE METHODS

CROSS REFERENCE TO RELATED APPLICATIONS

The present application is a 371 of International Application number PCT/EP2021/077057, filed Oct. 1, 2021, which is related to and claims the benefit of U.S. Provisional Ser. No. 63/086,830, filed Oct. 2, 2020, entitled "Treatment Protocols for Inhalation Delivery of Psychedelic Medications," U.S. Provisional Ser. No. 63/114,769, filed Nov. 17, 2020, entitled "Treatment Protocols for Inhalation of Psychedelic Medications," and U.S. Provisional Ser. No. 63/241,891, filed Sep. 8, 2021, entitled "Combination Drug Therapies," the entire contents of which are hereby incorporated by reference.

BACKGROUND

Field

Provided are methods for delivery of psychedelic medications by inhalation and systems and devices for performing those methods.

Description of the Related Art

Psychedelic compounds, both natural and synthetic, such as tryptamines, phenethylamines, ergolines and other derivatives, possess a range of valuable therapeutic properties that could be useful in treatments.

Psychedelics are named such because of their experiential effects on the user. Most often, the psychedelic experience acts to enhance the mood of the user when consumed. However, one potential psychological disorder resulting from the administration of psychedelics as therapeutics is the risk of a negative experience for the patient, presenting as acute psychedelic crisis, colloquially known as a "bad trip," in which the patient experiences feelings of remorse or distress.

The therapeutic index of many psychedelics is relatively narrow. Therefore, maximizing therapeutic benefits of potential drug candidate molecules requires fine-tuning of the dose and route of administration, along with dose titration, to reduce the side effects and improve safety.

In most cases the standard route of administration is by oral delivery, which is often times complicated by metabolic transformation leading to both decreased efficacy and increased toxicity. For some compounds, the oral route is completely ineffective. For example, a naturally occurring dimethyltryptamine (DMT) is orally inactive unless when combined with MAO inhibitors as in the folk medicine ayahuasca.

Inhalation methods of drug administration is generally geared toward relatively common medical situations including asthma, pain control or treatment of diabetes. Pulmonary delivery is attractive as a route for systemic administration due to fast absorption by the massive surface area of the alveolar region, the abundant vasculature and thin air-blood barrier, and the avoidance of first pass metabolism. The effectiveness of an aerosol therapy is largely dependent on how much of the medication will reach the intended site of deposition. The deposition pattern of the administered aerosol is determined mainly by the formulation and the delivery device. Accordingly, there is an unmet medical need for methods and devices to deliver psychedelic drugs by inhalation, where the dosage can be controlled, while delivering the drug systemically via the pulmonary system.

SUMMARY

Accordingly, one object is to provide methods for delivery of a psychedelic medication (or combination of medications including a psychedelic medication) via inhalation by the patient in need thereof.

A further object is to provide methods for delivery of a psychedelic medication (or combination of medications including a psychedelic medication) via inhalation, in order to rapidly deliver the psychedelic drug or derivative thereof to the blood stream, bypassing first-pass metabolism.

Another object is to provide a method for treatment of central nervous system disorders or psychological disorders by administration of a mixture of nitrous oxide and oxygen (or air).

A further object is to provide methods for delivery of psychedelic drugs by co-administration of the psychedelic drug and nitrous oxide by inhalation where the nitrous oxide acts a driving gas for nebulization of the psychedelic drug.

A further object is to provide medical devices for the coadministration by inhalation of a psychedelic drug and nitrous oxide.

A further object is to provide a nitrous oxide and psychedelic drug delivery device that can be remotely activated and regulated to control the dose and duration of treatment, thus providing at home treatments under supervision of the therapist/psychiatrist via telehealth, thus assisting with patient compliance in drug administration and helping to prevent overdosing.

These, and other objects, alone or in combinations, have been satisfied by the discovery of methods for delivering psychedelic drugs to a patient in need thereof comprising administering via inhalation of a psychedelic drug in the form of an aerosol, methods for treating a central nervous system (CNS) disorder or psychological disorder via inhalation of a psychedelic drug in the form of an aerosol, devices for delivery of psychedelic drug and nitrous oxide mixtures by inhalation, including with remote activation and control, and methods for treating a central nervous system (CNS) disorder or psychological disorder via inhalation of nitrous oxide/oxygen mixtures having an amount of nitrous oxide of 15 to 25% by volume of total gas.

Thus, the following embodiments, which are not intended to be limiting are disclosed:

Embodiment 1: A method of delivering a psychedelic drug to a patient in need thereof comprising administering an aerosol to the patient by inhalation, wherein the aerosol comprises the psychedelic drug in a carrier.

Embodiment 2. The method of Embodiment 1, wherein the carrier is air, oxygen, or a mixture of helium and oxygen.

Embodiment 3. The method of Embodiment 2, wherein the mixture of helium and oxygen is heated to about 50° C. to about 60° C.

Embodiment 4. The method of any one of Embodiments 1 to 3, wherein the psychedelic drug comprises one or more of dimethyltryptamine (DMT), 5-methoxy-dimethyltryptamine (5-MeO-DMT), or 5-hydroxy-dimethyltryptamine (5-OH-DMT).

Embodiment 5. The method of any one of Embodiments 1 to 3, wherein the psychedelic drug is psilocybin.

Embodiment 6. The method of any one of Embodiments 1 to 5, wherein the psychedelic drug is delivered to the patient's central nervous system via pulmonary absorption.

Embodiment 7. The method of Embodiment 2, wherein the carrier is a mixture of helium and oxygen.

Embodiment 8. The method of Embodiment 7, wherein the helium is present in the mixture of helium and oxygen at about 50%, 60%, 70%, 80% or 90% and the oxygen is present in the mixture of helium and oxygen at about 50%, 40%, 30%, or 10%.

Embodiment 9. The method of any one of Embodiments 1 to 8, further comprising administering a pretreatment inhalation therapy prior to administration of the aerosol comprising the psychedelic drug and the carrier.

Embodiment 10. The method of Embodiment 9, wherein the pretreatment comprises administering via inhalation a mixture of helium and oxygen heated to about 90° C. to about 120° C. to the patient.

Embodiment 11. The method of Embodiment 10 further comprising (i) administering via inhalation a mixture of helium and oxygen heated to about 90° C. to about 120° C. to the patient, and (ii) administering via inhalation to the patient an aerosol comprising the psychedelic drug and the mixture of helium and oxygen heated to about 50° C. to about 60° C.

Embodiment 12. The method of Embodiment 11, further comprising repeating steps (i) and (ii) 1 or more times.

Embodiment 13. The method of Embodiment 12, wherein steps (i) and (ii) are repeated from 1 to 5 times.

Embodiment 14. The method of Embodiment 12, wherein steps (i) and (ii) are repeated more than 5 times.

Embodiment 15. The method of Embodiment 6, wherein the psychedelic drug is delivered to the patient's central nervous system, providing an improvement in drug bioavailability by at least 25% as compared to oral delivery, increased Cmax by at least 25% as compared to oral delivery, reduced Tmax by at least 50% as compared to oral delivery, or a combination thereof.

Embodiment 16. The method of any one of Embodiments 1 to 15, wherein the aerosol is a mist.

Embodiment 17. The method of any one of Embodiments 1 to 16, wherein the aerosol is prepared by nebulization of the psychedelic drug.

Embodiment 18. The method of Embodiment 17, wherein the nebulization is performed with a member selected from the group consisting of jet nebulizers, ultrasonic nebulizers, breath-actuated nebulizers, and vibrating mesh nebulizers.

Embodiment 19. The method of Embodiment 17, wherein the nebulization is performed using nitrous oxide as a driving gas for entrainment of the nebulized psychedelic drug.

Embodiment 20. The method of Embodiment 19, wherein the nitrous oxide is present in a concentration of 15 to 25% of the volume of gas used. In some embodiments, the amount of the psychedelic drug to be administered can be reduced by about 2, 5, 10, 20, 30 or more percent when co-administered with nitrous oxide. In some embodiments, the co-administration of the psychedelic drug with nitrous oxide results in a decrease in the number or severity of side effects resulting from the administration of nitrous oxide or psychedelic drug.

Embodiment 21. The method of Embodiment 20, wherein the nitrous oxide is present in a concentration of 15 to 20% of the volume of gas used.

Embodiment 22. The method of Embodiment 19, wherein the aerosol is administered for 20 to 60 mins.

Embodiment 23. The method of Embodiment 22, wherein the aerosol is administered for 30 to 45 mins.

Embodiment 24. A method of treating a central nervous system (CNS) disorder or psychological disorder comprising administering, via inhalation, an aerosol comprising a psychedelic drug in a carrier.

Embodiment 25. The method of Embodiment 24, wherein the aerosol is a mist.

Embodiment 26. The method of Embodiment 24 or 25, wherein the carrier is air, oxygen, or a mixture of helium and oxygen.

Embodiment 27. The method of Embodiment 26, wherein the carrier is a mixture of helium and oxygen and the mixture of helium and oxygen is heated to about 50° C. to about 60° C. prior to administering the aerosol to the patient.

Embodiment 28. The method of any one of Embodiments 24 to 27, wherein the CNS disorder is at least one member selected from the group consisting of melancholic depression, atypical depression, dysthymia, anxiety disorder, obsessive compulsive disorder, addiction disorder, alcohol use disorder, opioid use disorder, amphetamine use disorder, nicotine use disorder, cocaine use disorder, post-traumatic stress disorder (PTSD), major depressive disorder (MDD), treatment-resistant depression (TRD), suicidal ideation and suicide attempts, bipolar I disorder, bipolar II disorder, cyclothymic disorder, obsessive-compulsive disorder (OCD), generalized anxiety disorder (GAD), social anxiety disorder, Alzheimer's disease, cluster headache, migraine headaches, attention deficit hyperactivity disorder (ADHD), pain and neuropathic pain, aphantasia, childhood-onset fluency disorder, major neurocognitive disorder, mild neurocognitive disorder, sexual dysfunction, gambling disorder, eating disorder, anorexia nervosa, bulimia nervosa, binge-eating disorder, paraphilic disorders, pedophilic disorder, exhibitionistic disorder, voyeuristic disorder, fetishistic disorder, sexual masochism disorder, sexual sadism disorder, and transvestic disorder.

Embodiment 29. The method of any one of Embodiments 24 to 28, wherein the aerosol is prepared by nebulization of the psychedelic drug.

Embodiment 30. The method of Embodiment 28, wherein the nebulization is performed with a member selected from the group consisting of jet nebulizers, ultrasonic nebulizers, breath-actuated nebulizers, and vibrating mesh nebulizers.

Embodiment 31. The method of Embodiment 28, wherein the nebulization is performed using nitrous oxide as a driving gas for entrainment of the nebulized psychedelic drug.

Embodiment 32. The method of Embodiment 31, wherein the nitrous oxide is present in a concentration of 15 to 25% of the volume of gas used.

Embodiment 33. The method of Embodiment 32, wherein the nitrous oxide is present in a concentration of 15 to 20% of the volume of gas used.

Embodiment 34. The method of Embodiment 31, wherein the aerosol is administered for 20 to 60 mins.

Embodiment 35. The method of Embodiment 34, wherein the aerosol is administered for 30 to 45 mins.

Embodiment 36. A method of delivering a psychedelic drug to a patient in need thereof comprising administering the psychedelic drug to the patient by inhalation via a dry powder inhaler, wherein the dry powder inhaler delivers a dry powder comprising the psychedelic drug.

Embodiment 37. The method of Embodiment 36, wherein the dry powder comprises a particulate carrier having the psychedelic drug on a surface thereof.

Embodiment 38. The method of Embodiment 37, wherein the psychedelic drug is releasably absorbed onto a surface of the particulate carrier, such that upon inhalation by the patient, the psychedelic drug is released from the particulate carrier within the patient.

Embodiment 39. The method of Embodiment 36, wherein the dry powder is formed of the psychedelic drug in solid particulate form.

Embodiment 40. The method of any one of Embodiments 36 to 39, wherein the psychedelic drug comprises one or more of dimethyltryptamine (DMT), 5-methoxy-dimethyltryptamine (5-MeO-DMT), or 5-hydroxy-dimethyltryptamine (5-OH-DMT).

Embodiment 41. The method of any one of Embodiments 36 to 39, wherein the psychedelic drug is psilocybin.

Embodiment 42. The method of any one of Embodiments 36 to 41, wherein the psychedelic drug is delivered to the patient's central nervous system via pulmonary absorption.

Embodiment 43. The method of any one of Embodiments 36 to 42, further comprising administering a pretreatment inhalation therapy prior to administration of the psychedelic drug to the patient.

Embodiment 44. The method of Embodiment 43, wherein the pretreatment comprises administering via inhalation a mixture of helium and oxygen heated to about 90° C. to about 120° C. to the patient.

Embodiment 45. The method of Embodiment 44 further comprising (i) administering via inhalation a mixture of helium and oxygen heated to about 90° C. to about 120° C. to the patient, and (ii) administering via inhalation to the patient the psychedelic drug.

Embodiment 46. The method of Embodiment 45, further comprising repeating steps (i) and (ii) 1 or more times.

Embodiment 47. The method of Embodiment 46, wherein steps (i) and (ii) are repeated from 1 to 5 times.

Embodiment 48. The method of Embodiment 46, wherein steps (i) and (ii) are repeated more than 5 times.

Embodiment 49. The method of any one of Embodiments 36 to 48, wherein the psychedelic drug is delivered to the patient's central nervous system, providing an improvement in drug bioavailability by at least 25% as compared to oral delivery, increased Cmax by at least 25% as compared to oral delivery, reduced Tmax by at least 50% as compared to oral delivery, or a combination thereof.

Embodiment 50. An inhalation delivery device for delivery of a combination of nitrous oxide and a psychedelic drug by inhalation by a patient in need thereof, comprising:

an inhalation outlet portal for administration of the combination of nitrous oxide and the psychedelic drug to the patient;

a container configured to deliver nitrous oxide gas to the inhalation outlet portal; and a device configured to generate and deliver an aerosol comprising the psychedelic drug to the inhalation outlet portal.

Embodiment 51. The inhalation delivery device of Embodiment 50, wherein the inhalation outlet portal is selected from a mouthpiece or a mask covering the patient's nose and mouth.

Embodiment 52. The inhalation delivery device of Embodiment 50 or 51, wherein the device configured to generate and deliver the aerosol to the inhalation outlet portal is a nebulizer.

Embodiment 53. The inhalation delivery device of Embodiment 52, wherein the nebulizer is a jet nebulizer and the nitrous oxide gas acts as a driving gas for the jet nebulizer.

Embodiment 54. The inhalation delivery device of any one of Embodiments 50 to 53, further comprising electronics configured to provide remote activation and operational control of the inhalation delivery device.

Embodiment 55. A method of treating a central nervous system (CNS) disorder or psychological disorder comprising administering, via inhalation, a gas mixture of nitrous oxide and oxygen or air, wherein the nitrous oxide is present in an amount of from 15 to 25% by volume of total gas mixture.

Embodiment 56. The method of Embodiment 55, wherein the nitrous oxide is present in an amount of from 15 to 20% by volume of total gas mixture.

Embodiment 57. The method of Embodiment 55 or 56, wherein the administering is performed for a period of 20 to 60 mins.

Embodiment 58. The method of Embodiment 57, wherein the administering is performed for a period of 30 to 45 mins.

Embodiment 59. The method of one of Embodiments 55 to 58, wherein the psychological disorder is acute psychedelic crisis.

DETAILED DESCRIPTION

The following detailed description is merely exemplary in nature and is not intended to limit the described compositions or methods.

One embodiment provides a method of delivering a psychedelic drug to a patient in need thereof comprising administering a psychedelic drug or derivative thereof dissolved in an aerosol, such as a mist, via inhalation. In some embodiments the aerosol is generated without externally added heat (this does not exclude minor temperature increases caused by the formation of the aerosol itself, such as with a vibrating mesh or other nebulizer. However, such minor temperature increases can often be offset by vaporization of the drug, which results in cooling of the composition). The psychedelic drug can be any desired drug providing psychedelic effects, including, but not limited to, phenethylamine derivatives including, but not limited to, MDMA, MDEA, MBDB, TMA, DOM, DOET, DOI, DOC, tryptamine derivatives, including, but not limited to, DMT, 5-MeO-DMT, psilocybin, psilocin, compounds of Formula (I), Formula (II), Formula (II-a), Formula (II-b), Formula (II-c), Formula (II-d), Formula III, Formula (III-a), Formula (IV), Formula (IV-a), Formula (IV-b), Formula (V), Formula (V-a), Formula (V-b), Formula (VI), Formula (VI-a), and Formula (VI-b) described herein, any exemplary compounds described herein, and combinations thereof. In an embodiment, the psychedelic drug or derivative thereof can be delivered as an aerosol, such as a mist, with a carrier, such as air, oxygen, or a mixture of helium and oxygen. In a further embodiment, the carrier can be a mixture of helium and oxygen heated to about 50° C. to about 60° C.

In one embodiment, the psychedelic drug can comprise one or more of dimethyltryptamine (DMT), 5-methoxy-dimethyltryptamine (5-MeO-DMT), 5-hydroxy-dimethyl-tryptamine (5-OH-DMT), or derivatives thereof. In a further embodiment, the psychedelic drug can be psilocybin or derivatives thereof. Additionally, by administration via inhalation, the psychedelic drug can be delivered systemically to the patient's central nervous system. The air, oxygen, or mixture of helium and oxygen can be heated to about 55° C. to about 56° C. When a mixture of helium and oxygen is used as the carrier, the helium can be present in the mixture of oxygen and helium at about 50%, 60%, 70%, 80% or 90% and the oxygen can be present in the mixture at about 50%, 40%, 30%, 20%, or 10%.

The method can further comprise administering a pre-treatment inhalation therapy prior to administration of the aerosol comprising the psychedelic drug or derivative thereof. The pretreatment can comprise administering via inhalation of a mixture of helium and oxygen heated to about 90° C. to about 120° C. (e.g., about 90, 100, 110, or 120° C.) to the patient.

The method can comprise (i) administering via inhalation a mixture of helium and oxygen heated to about 90° C. to about 120° C. (e.g., about 90, 100, 110, or 120° C.) to the patient, followed by (ii) administering via inhalation a mixture of helium and oxygen heated to about 50° C. to about 60° C. (e.g., about 50, 52, 53, 56, 58, or 60° C.) and the aerosol comprising the psychedelic drug or derivative thereof to the patient and then repeating steps (i) and (ii). Steps (i) and (ii) can be repeated 1, 2, 3, 4, 5, or more times.

One embodiment provides a method of treating a central nervous system (CNS) disorder or psychological disorder comprising administering, via inhalation, a psychedelic drug or derivative thereof in the form of an aerosol, such as a mist.

The psychedelic drug or derivative thereof can be delivered as an aerosol along with a carrier selected from air, oxygen, or a mixture of helium and oxygen. The mixture of helium and oxygen can be heated to about 50° C. to about 60° C. (e.g., about 50, 52, 53, 56, 58, or 60° C.) prior to administering the aerosol comprising the psychedelic drug or derivative thereof to the patient.

The central nervous system or psychological disorder can be, for example, melancholic depression, atypical depression, dysthymia, anxiety disorder, obsessive compulsive disorder, addiction (narcotic addiction, tobacco addiction, opioid addiction), alcoholism, post-traumatic stress disorder (PTSD), major depressive disorder (MDD), treatment-resistant depression (TRD), suicidal ideation and suicide attempts, bipolar and related disorders, generalized anxiety disorder (GAD), social anxiety disorder, anorexia nervosa, bulimia nervosa, Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, sexual dysfunction, gambling disorder, eating disorders such as anorexia nervosa, bulimia nervosa, binge-eating disorder, etc., and paraphilic disorders such as, for example, pedophilic disorder, exhibitionistic disorder, voyeuristic disorder, fetishistic disorder, sexual masochism or sadism disorder, and transvestic disorder, etc.

In one embodiment the psychedelic drug is delivered by inhalation to the patient's central nervous system resulting in an improvement in drug bioavailability by at least 25% (e.g., at least about 25, 30, 35, 40, 45, 50% or more) as compared to oral delivery, increased $C_{max}$ by at least 25% (e.g., at least about 25, 30, 35, 40, 45, 50% or more) as compared to oral delivery, reduced $T_{max}$ by at least 50% (e.g., reduced by at least 50, 60, 70, 80% or more) as compared to oral delivery, or a combination thereof.

Good aqueous solubility of most psychedelics including e.g., DMT (in the salt form) makes inhalation of an aerosol, such as a mist, a possible route of administration. However, inhalation of a mist is mainly used for local rather than systemic drug delivery and faces multiple challenges related to inconsistent and incomplete dose delivery, variability in the breathing pattern, deposition of the dose in the upper respiratory tract, etc. Methods are provided herein for mist inhalation administration of psychedelic drugs.

Psychedelic Drugs

Therapeutic agents of the present disclosure can include any desired psychedelic drugs or derivatives thereof. The term "psychedelic," "psychedelic compound," "psychedelic agent," or "psychedelic drug" as used herein can encompass a number of compounds including serotonin 5-$HT_{2A}$ receptor agonists (e.g., lysergic acid diethylamide (LSD)), empathogenic agents (i.e., serotonin (5-HT) releasing agents; e.g., 3,4-methylenedioxymethamphetamine (MDMA)), and dissociative agents (i.e., N-Methyl-D-aspartate (NMDA) receptor agonists; e.g., nitrous oxide, ketamine and dextromethorphan). Most psychedelic drugs fall within the following groups: tryptamines, phenethylamines, or lysergamides. These drugs all activate serotonin 5-$HT_{2A}$ receptors, which modulate the activity of key circuits in the brain involved with sensory perception and cognition. Tryptamines include, for example, 5-methoxy-dimethyltryptamine (5-MeO-DMT), 5-hydroxy-dimethyltryptamine (5-OH-DMT), dimethyltryptamine (DMT), or derivatives thereof. 5-OH-DMT is also known as bufotenine. 5-MeO-DMT is a prodrug to bufotenine via demethylation. DMT is also known as N,N-Dimethyltryptamine and is a primary active constituent of ayahuasca. Other psychedelic drugs are described below.

A derivative includes any compound that is made from a psychedelic drug such as one of the psychedelic drugs described herein, for example, by replacing one atom in the psychedelic drug with another atom or group of atoms, rearranging two or more atoms in the psychedelic drug, ionizing a psychedelic drug, or creating a salt of one of the psychedelic drug.

Unless clearly indicated to the contrary, the term "derivative" does not mean that the derivative is synthesized using the parent compound as a starting material or as an intermediate, although in some cases, the derivative can be synthesized from the parent. In an embodiment, a derivative of a psychedelic drug has therapeutic activity.

As used herein, a "5-HT2A agonist" refers to a compound that increases the activity of a 5-hydroxytryptamine 2A receptor. Examples of such agonists further include, but are not limited to, psilocybin and derivatives thereof, DOI (±)-1-(2,5-dimethoxyphenyl)-2-aminopropane hydrochloride; (R)-DOI ((R)-1-(2,5-dimethoxy-4-iodophenyl)-2-aminopropane) (greater than 95% R enantiomer) (a substituted amphetamine); LA-SS-Az (2'S,4'S)-(+)-9,10-Didehydro-6-methylergoline-8B-(trans-2,4-dimethylazetidide) (a complex tryptamine); 2C-BCB (4-Bromo-3,6-dimethoxybenzocyclobuten-1-yl)methylamine; 3,4,5-trimethoxyphenethylamine (mescaline); or ibogaine. Derivatives of psilocybin include, for example, [3-[2-Dimethylaminoethyl)-1H-indol-4-yl] dihydrogen phosphate, 4-hydroxy-N,N-dimethyltryptamine, 3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, 4-hydroxytryptamine, [3-(2-trimethylaminoethyl)-1H-indol-4-yl] dihydrogen phosphate, or 4-hydroxy-N,N,N-trimethyltryptamine.

Other psychedelic drugs include, for example, tryptamine derivatives such as Formula (I) below or an optically pure stereoisomer, pharmaceutically acceptable salt, solvate, or prodrug thereof:

Formula (I)

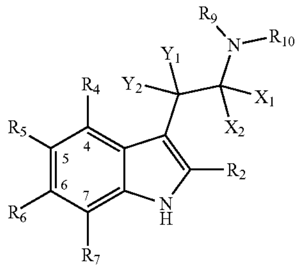

For some embodiments, $X_1$ and $X_2$ are independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, For some embodiments, $Y_1$ and $Y_2$ are independently selected from hydrogen and deuterium, For some embodiments, $R_2$ is independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, For some embodiments, $R_4$ and $R_5$ are independently selected from hydrogen, hydroxyl, and unsubstituted or substituted alkoxy, For some embodiments, $R_6$ and $R_7$ are selected from hydrogen and halogen, For some embodiments, $R_9$ and $R_{10}$ are independently selected from unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, and For some embodiments, at least one of X1, X2, Y1, Y2, R2, R4, R5, R6, and R7 is deuterium. Psychedelic drugs can include a compound according to Formula (II) or an optically pure stereoisomer, pharmaceutically acceptable salt, solvate, or prodrug thereof, wherein $X_1$ and $X_2$ are deuterium.

Formula (II)

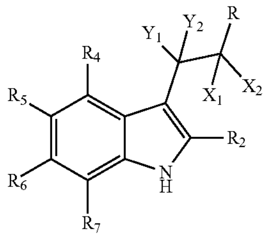

For some embodiments, $Y_1$ and $Y_2$ are independently selected from hydrogen and deuterium, For some embodiments, R is

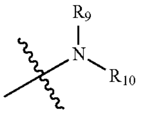

or

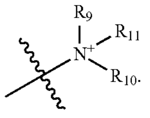

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ and $R_5$ are independently selected from hydrogen, deuterium, hydroxyl, unsubstituted or substituted alkoxy, and unsubstituted or substituted phosphoryloxy.

For some embodiments, $R_6$ and $R_7$ are selected from hydrogen, deuterium, and halogen.

For some embodiments, $R_9$, $R_{10}$, and $R_{11}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Psychedelic drugs can include a compound according to Formula (II-a) or an optically pure stereoisomer, pharmaceutically acceptable salt, solvate, or prodrug thereof, wherein $X_1$ and $X_2$ are deuterium, and $Y_1$ and $Y_2$ are hydrogen.

Formula (II-a)

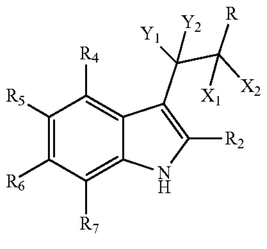

For some embodiments, R is

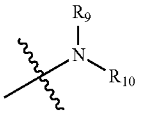

or

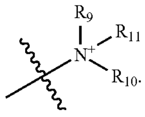

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ and $R_5$ are independently selected from hydrogen, deuterium, hydroxyl, unsubstituted or substituted alkoxy, and unsubstituted or substituted phosphoryloxy.

For some embodiments, $R_6$ and $R_7$ are selected from hydrogen, deuterium, and halogen.

For some embodiments, $R_9$, $R_{10}$, and $R_{11}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Psychedelic drugs can include a compound according to Formula (II-b) or an optically pure stereoisomer, pharmaceutically acceptable salt, solvate, or prodrug thereof, wherein $X_1$ and $X_2$ are deuterium, $Y_1$ and $Y_2$ are hydrogen, and R is

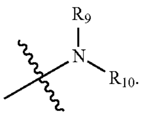

Formula (II-b)

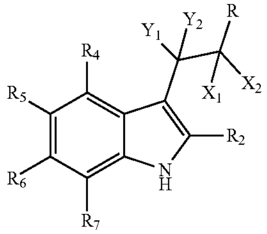

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ and $R_5$ are independently selected from hydrogen, deuterium, hydroxyl, unsubstituted or substituted alkoxy, and unsubstituted or substituted phosphoryloxy.

For some embodiments, $R_6$ and $R_7$ are selected from hydrogen, deuterium, and halogen.

For some embodiments, $R_9$ and $R_{10}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Psychedelic drugs can include a compound according to Formula (II-c) or an optically pure stereoisomer, pharmaceutically acceptable salt, solvate, or prodrug thereof, wherein $X_1$ and $X_2$ are deuterium, $Y_1$ and $Y_2$ are hydrogen, and R is

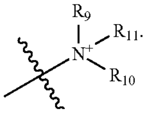

Formula (II-c)

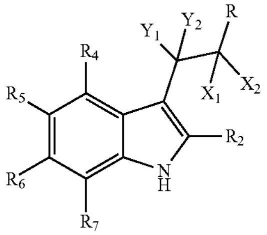

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ and $R_5$ are independently selected from hydrogen, deuterium, hydroxyl, unsubstituted or substituted alkoxy, and unsubstituted or substituted phosphoryloxy.

For some embodiments, $R_6$ and $R_7$ are selected from hydrogen, deuterium, and halogen.

For some embodiments, $R_9$, $R_{10}$, and $R_{11}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Psychedelic drugs can include a compound according to Formula (II-d) or an optically pure stereoisomer, pharmaceutically acceptable salt, solvate, or prodrug thereof, wherein $X_1$ and $X_2$ are deuterium, $Y_1$ and $Y_2$ are hydrogen, and R is

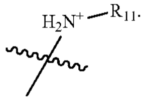

Formula (II-d)

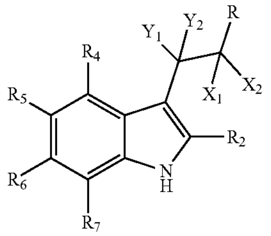

For some embodiments, $R_2$ is independently selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

For some embodiments, $R_4$ and $R_5$ are independently selected from hydrogen, deuterium, hydroxyl, unsubstituted or substituted alkoxy, and unsubstituted or substituted phosphoryloxy.

For some embodiments, $R_6$ and $R_7$ are selected from hydrogen, deuterium, and halogen.

For some embodiments, $R_{11}$ is independently selected from unsubstituted or substituted alkyl, unsubstituted or substituted allyl, unsubstituted or substituted alkenyl, unsubstituted or substituted alkynyl, unsubstituted or substituted aryl, and unsubstituted or substituted heterocycloalkyl, unsubstituted or substituted aryl, and unsubstituted or substituted hereoarul.

For some embodiments the compound is selected from the group consisting of:

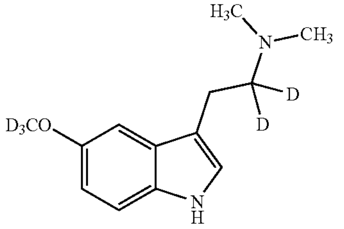

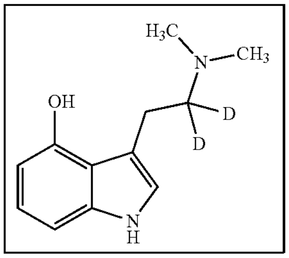

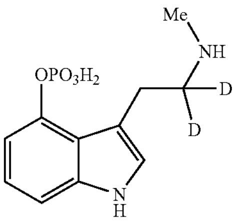

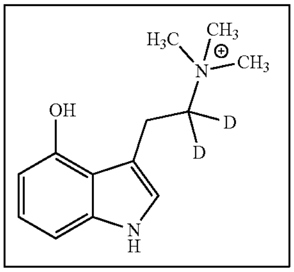

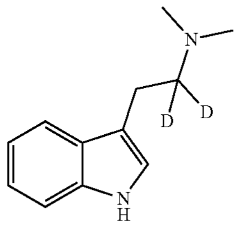

-continued

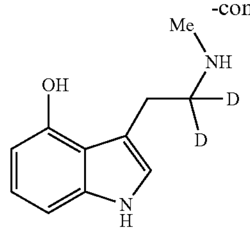

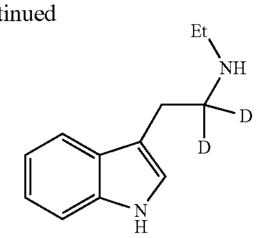

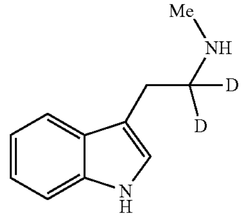

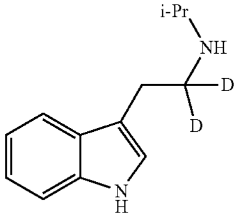

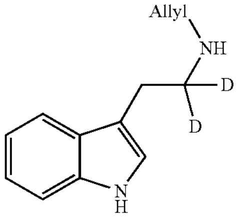

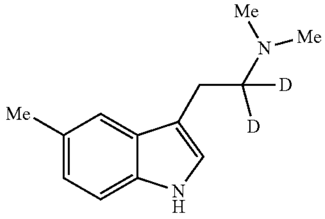

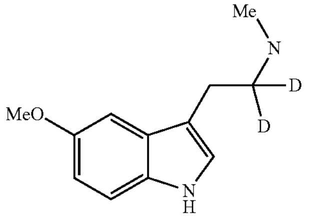

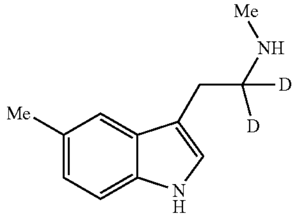

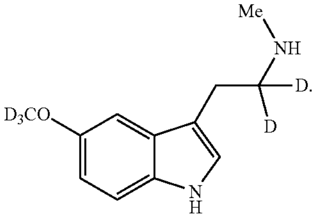

For some embodiments, the compounds described herein, e.g., compounds of Formula (II), Formula (II-a), Formula (II-b), Formula (II-c), and Formula (II-d), have at least one of $R_2$, $R_4$, $R_5$, $R_6$, and $R_7$ is deuterium or substituted with a deuterium.

For some embodiments, $R_6$ and/or $R_7$ of the compounds described herein, e.g., compounds of Formula (II), Formula (II-a), Formula (II-b), Formula (II-c), and Formula (II-d), is halogen.

For some embodiments, $R_4$ and/or $R_5$ of the compounds described herein, e.g., compounds of Formula (II), Formula (II-a), Formula (II-b), Formula (II-c), and Formula (II-d), is deuterium or substituted with a deuterium.

Psychedelic drugs can include phenethylamine derivatives such as a compound according to Formula (III) below or an optically pure stereoisomer, pharmaceutically acceptable salt, solvate, or prodrug thereof:

Formula (III)

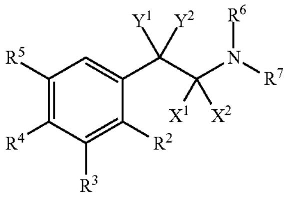

For some embodiments, $X^1$ and $X^2$ are independently selected from hydrogen, deuterium, and unsubstituted or substituted $C_1$-$C_6$ alkyl.

For some embodiments, $Y^1$ and $Y^2$ are independently selected from hydrogen and deuterium.

For some embodiments, $R^2$ and $R^3$ are independently selected from hydrogen, deuterium, halogen, unsubstituted or substituted $C_1$-$C_6$ alkyl, and —$OR^a$.

For some embodiments, $R^4$ and $R^5$ are independently selected from hydrogen, deuterium, halogen, —$OR^a$, and —$SR^a$, or $R^4$ and $R^5$ together with the atoms to which they are attached form an unsubstituted or substituted heterocycloalkyl or an unsubstituted or substituted heteroaryl.

For some embodiments, $R^6$ and $R^7$ are independently selected from hydrogen and unsubstituted or substituted $C_1$-$C_6$ alkyl.

For some embodiments, each $R^a$ is independently selected from hydrogen, deuterium, and unsubstituted or substituted $C_1$-$C_6$ alkyl.

For some embodiments, at least one of $X^1$, $X^2$, $Y^1$, $Y^2$, $R^2$, $R^4$, $R^5$, $R^6$, and $R^7$ is deuterium.

For some embodiments, $R^4$ is hydrogen, deuterium, halogen, —$OR^a$, and —$SR^a$, and $R^a$ is $C_1$-$C_6$ alkyl, which is unsubstituted or substituted with one or more deuteriums.

For some embodiments, $R^5$ is hydrogen, deuterium, halogen, —$OR^a$, and —$SR^a$, and $R^a$ is $C_1$-$C_6$ alkyl, which is unsubstituted or substituted with one or more deuteriums.

For some embodiments, $R^4$ is —$OCH_3$, —$OCD_3$, —Br·—$SCH_3$, —$SCH_2CH_3$, or —$SCH_2CH_2CH_3$, and/or $R^5$ is hydrogen, —OMe, or —$OCD_3$.

For some embodiments, $R^4$ and $R^5$ together with the atoms to which they are attached form a heterocycloalkyl or a heteroaryl.

For some embodiments, the compound can have a structure according to Formula (III-a) as shown below.

Formula (III-a)

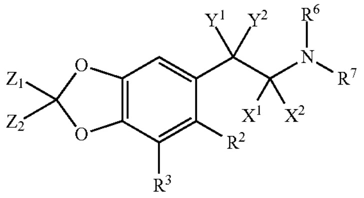

For some embodiments, each $Z_1$ and $Z_2$ is independently hydrogen or deuterium.

For some embodiments, $R^3$ is independently selected from hydrogen, deuterium, halogen, unsubstituted or substituted $C_1$-$C_6$ alkyl, and —$OR^a$.

For some embodiments, $X^1$ and $X^2$ are independently selected from hydrogen, deuterium, and unsubstituted or substituted $C_1$-$C_6$ alkyl.

For some embodiments, $Y^1$ and $Y^2$ are independently selected from hydrogen and deuterium.

For some embodiments, $R^6$ and $R^7$ are independently selected from hydrogen and unsubstituted or substituted $C_1$-$C_6$ alkyl.

For some embodiments, each $R^a$ is independently selected from hydrogen, deuterium, and unsubstituted or substituted $C_1$-$C_6$ alkyl.

For some embodiments, at least one of $Z_1$, $Z_2$, $X^1$, $X^2$, $Y^1$, $Y^2$, $R^6$, and $R^7$ is deuterium.

For some embodiments, each $R^6$ and $R^7$ is independently hydrogen, —$CH_3$, or —$OCD_3$.

For some embodiments the compound can be

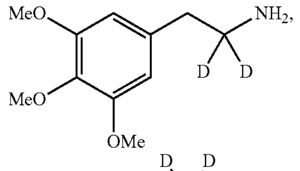

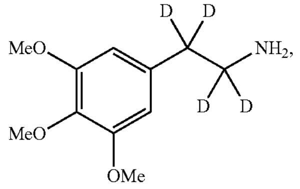

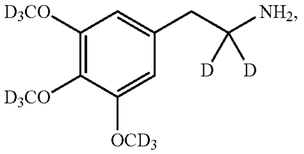

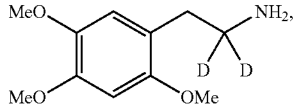

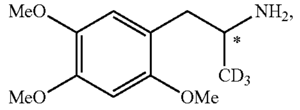

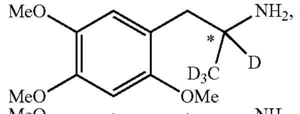

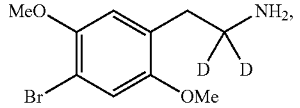

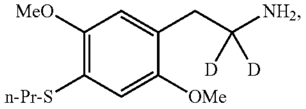

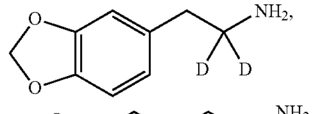

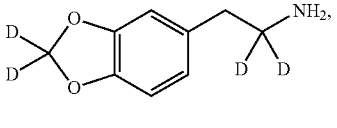

-continued

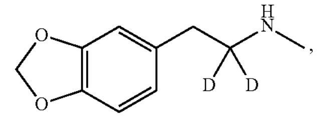

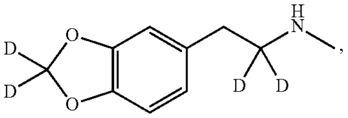

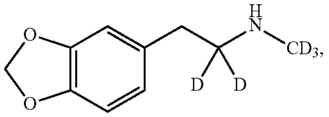

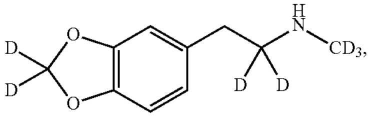

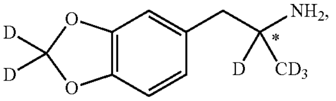

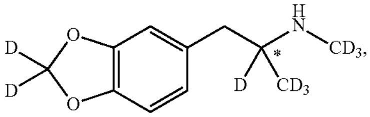

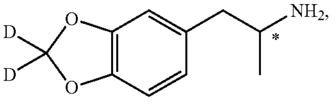

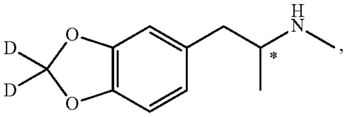

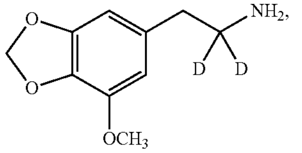

or

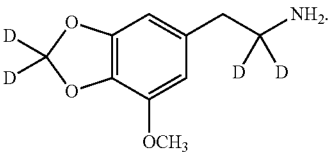

Psychedelic drugs can also include N-substituted phenethylamines (NSPs) and derivatives thereof. NSPs can include a compound according to Formula (IV) or an optically pure stereoisomer, pharmaceutically acceptable salt, solvate, or prodrug thereof.

Formula (IV)

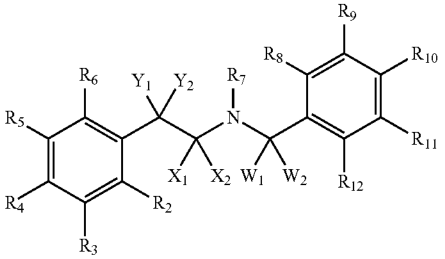

For some embodiments, $R^2$ and $R^3$ are independently selected from hydrogen, deuterium, cyano, halogen, unsubstituted or substituted $C_1$-$C_6$ alkyl, —$OR^a$, and —$SR^a$, or $R_2$ and $R_3$ together with the atoms to which they are attached optionally form an unsubstituted or substituted cycloalkyl, aryl, heterocycloalkyl, or heteroaryl.

For some embodiments, $R_4$ is selected from hydrogen, deuterium, cyano, halogen, unsubstituted or substituted $C_1$-$C_6$ alkyl, —$OR^a$, and —$SR^a$.

For some embodiments, $R_5$ and $R_6$ are independently selected from hydrogen, deuterium, cyano, halogen, unsubstituted or substituted $C_1$-$C_6$ alkyl, —$OR^a$, and —$SR^a$, or $R_5$ and $R_6$ together with the atoms to which they are attached optionally form an unsubstituted or substituted cycloalkyl, aryl, heterocycloalkyl, or heteroaryl.

For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl. For some embodiments, $R_8$, $R_9$, and $R_{10}$ are independently selected from hydrogen, deuterium, hydroxyl, cyano, halogen, unsubstituted or substituted $C_1$-$C_6$ alkyl, —$OR^a$, and —$SR^a$.

For some embodiments, $R_{11}$ and $R_{12}$ are independently selected from hydrogen, deuterium, hydroxyl, cyano, halogen, unsubstituted or substituted $C_1$-$C_6$ alkyl, —$OR^a$, and —$SR^a$, or $R_{11}$ and $R_{12}$ together with the atoms to which they are attached form an unsubstituted or substituted cycloalkyl, aryl, heterocycloalkyl, or heteroaryl.

For some embodiments, each $R^a$ is independently selected from hydrogen, deuterium, and unsubstituted or substituted $C_1$-$C_6$ alkyl.

For some embodiments, at least one of $W_1$, $W_2$, $X_1$, $X_2$, $Y_1$, $Y_2$, $R_2$, $R_3$, $R_4$, $R_5$, $R_6$, $R_7$, $R_8$, $R_9$, $R_{10}$, $R_{11}$, $R_{12}$ is deuterium or substituted with deuterium.

NSPs can include a compound according to Formula (IV-a) or an optically pure stereoisomer, pharmaceutically acceptable salt, solvate, or prodrug thereof.

Formula (IV-a)

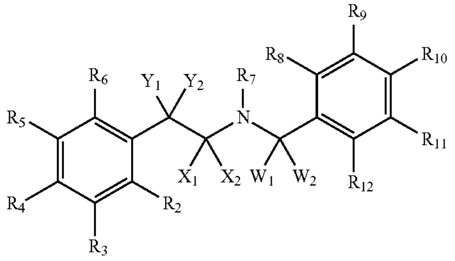

For some embodiments, $R_2$ and $R_3$ are independently selected from hydrogen, deuterium, cyano, halogen, unsubstituted or substituted $C_1$-$C_6$ alkyl, —$OR^a$, and —$SR^a$, or $R_2$ and $R_3$ together with the atoms to which they are attached optionally form an unsubstituted or substituted cycloalkyl, aryl, heterocycloalkyl, or heteroaryl.

For some embodiments, $R_4$ is selected from hydrogen, deuterium, cyano, halogen, unsubstituted or substituted $C_1$-$C_6$ alkyl, —$OR^a$, and —$SR^a$.

For some embodiments, $R_5$ and $R_6$ are independently selected from hydrogen, deuterium, cyano, halogen, unsubstituted or substituted $C_1$-$C_6$ alkyl, —$OR^a$, and —$SR^a$, or $R_5$ and $R_6$ together with the atoms to which they are attached optionally form an unsubstituted or substituted cycloalkyl, aryl, heterocycloalkyl, or heteroaryl.

For some embodiments, $W_1$ and $W_2$ are independently selected from hydrogen, deuterium, and unsubstituted or substituted $C_1$-$C_6$ alkyl.

For some embodiments, $X_1$ and $X_2$ are deuterium.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl. For some embodiments, $R_8$, $R_9$, and $R_{10}$ are independently selected from hydrogen, deuterium, hydroxyl, cyano, halogen, unsubstituted or substituted $C_1$-$C_6$ alkyl, —$OR^a$, and —$SR^a$.

For some embodiments, $R_{11}$ and $R_{12}$ are independently selected from hydrogen, deuterium, hydroxyl, cyano, halogen, unsubstituted or substituted $C_1$-$C_6$ alkyl, —$OR^a$, and —$SR^a$, or $R_{11}$ and $R_{12}$ together with the atoms to which they are attached form an unsubstituted or substituted cycloalkyl, aryl, heterocycloalkyl, or heteroaryl.

For some embodiments, each $R^a$ is independently selected from hydrogen, deuterium, and unsubstituted or substituted $C_1$-$C_6$ alkyl.

For some embodiments, at least one of $W_1$, $W_2$, $Y_1$, $Y_2$, $R_2$, $R_3$, $R_4$, $R_5$, $R_6$, $R_7$, $R_8$, $R_9$, $R_{10}$, $R_{11}$, $R_{12}$ is deuterium or substituted with deuterium.

NSPs can include a compound according to Formula (IV-b) or an optically pure stereoisomer, pharmaceutically acceptable salt, solvate, or prodrug thereof.

Formula (IV-b)

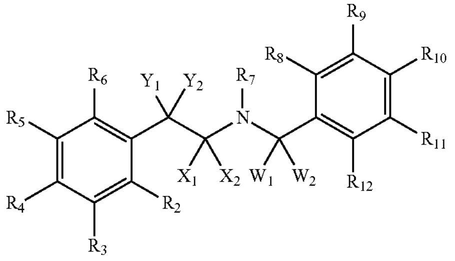

For some embodiments, $R_2$ and $R_3$ are independently selected from hydrogen, deuterium, cyano, halogen, unsubstituted or substituted $C_1$-$C_6$ alkyl, —$OR^a$, and —$SR^a$, or $R_2$ and $R_3$ together with the atoms to which they are attached optionally form an unsubstituted or substituted cycloalkyl, aryl, heterocycloalkyl, or heteroaryl.

For some embodiments, $R_4$ is selected from hydrogen, deuterium, cyano, halogen, unsubstituted or substituted $C_1$-$C_6$ alkyl, —$OR^a$, and —$SR^a$.

For some embodiments, $R_5$ and $R_6$ are independently selected from hydrogen, deuterium, cyano, halogen, unsubstituted or substituted $C_1$-$C_6$ alkyl, —$OR^a$, and —$SR^a$, or $R_5$ and $R_6$ together with the atoms to which they are attached optionally form an unsubstituted or substituted cycloalkyl, aryl, heterocycloalkyl, or heteroaryl.

For some embodiments, $W_1$ and $W_2$ are deuterium.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl. For some embodiments, $R_8$, $R_9$, and $R_{10}$ are independently selected from hydrogen, deuterium, hydroxyl, cyano, halogen, unsubstituted or substituted $C_1$-$C_6$ alkyl, —$OR^a$, and —$SR^a$.

For some embodiments, $R_{11}$ and $R_{12}$ are independently selected from hydrogen, deuterium, hydroxyl, cyano, halogen, unsubstituted or substituted $C_1$-$C_6$ alkyl, —$OR^a$, and —$SR^a$, or $R_{11}$ and $R_{12}$ together with the atoms to which they are attached form an unsubstituted or substituted cycloalkyl, aryl, heterocycloalkyl, or heteroaryl.

For some embodiments, each $R^a$ is independently selected from hydrogen, deuterium, and unsubstituted or substituted $C_1$-$C_6$ alkyl.

For some embodiments, at least one of $X_1$, $X_2$, $Y_1$, $Y_2$, $R_2$, $R_3$, $R_4$, $R_5$, $R_6$, $R_7$, $R_8$, $R_9$, $R_{10}$, $R_{11}$, $R_{12}$ is deuterium or substituted with deuterium.

NSPs can include a compound according to Formula (V) or an optically pure stereoisomer, pharmaceutically acceptable salt, solvate, or prodrug thereof.

Formula (V)

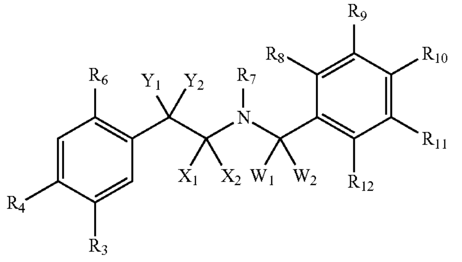

For some embodiments, $R_3$ and $R_6$ are —$OR^a$.

For some embodiments, $R_4$ is selected from hydrogen, deuterium, cyano, halogen, unsubstituted or substituted $C_1$-$C_6$ alkyl, —$OR^a$, and —$SR^a$.

For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl.

For some embodiments, $R_8$, $R_9$, and $R_{10}$ are independently selected from hydrogen, deuterium, hydroxyl, cyano, halogen, unsubstituted or substituted $C_1$-$C_6$ alkyl, —$OR^a$, and —$SR^a$.

For some embodiments, $R_{11}$ and $R_{12}$ are independently selected from hydrogen, deuterium, hydroxyl, cyano, halogen, unsubstituted or substituted $C_1$-$C_6$ alkyl, —$OR^a$, and —$SR^a$, or $R_{11}$ and $R_{12}$ together with the atoms to which they are attached form an unsubstituted or substituted cycloalkyl, aryl, heterocycloalkyl, or heteroaryl.

For some embodiments, each $R^a$ is independently selected from hydrogen, deuterium, and unsubstituted or substituted $C_1$-$C_6$ alkyl.

For some embodiments, at least one of $W_1$, $W_2$, $X_1$, $X_2$, $Y_1$, $Y_2$, $R_3$, $R_4$, $R_6$, $R_7$, $R_8$, $R_9$, $R_{10}$, $R_{11}$, $R_{12}$ is deuterium or substituted with deuterium.

NSPs can include a compound according to Formula (V-a) or an optically pure stereoisomer, pharmaceutically acceptable salt, solvate, or prodrug thereof.

Formula (V-a)

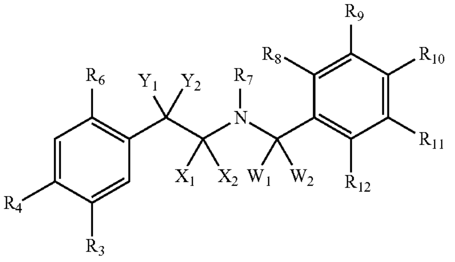

For some embodiments, $R_3$ and $R_6$ are —$OR^a$.

For some embodiments, $R_4$ is selected from cyano, halogen, unsubstituted or substituted $C_1$-$C_6$ alkyl, —$OR^a$, and —$SR^a$.

For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl.

For some embodiments, $R_8$, $R_9$, $R_{10}$, and $R_{11}$ are independently selected from hydrogen and deuterium.

For some embodiments, $R_{12}$ is selected from hydroxyl, halogen, unsubstituted or substituted $C_1$-$C_6$ alkyl, —$OR^a$, and —$SR^a$.

For some embodiments, each $R^a$ is independently selected from hydrogen, deuterium, and unsubstituted or substituted $C_1$-$C_6$ alkyl.

For some embodiments, at least one of $W_1$, $W_2$, $X_1$, $X_2$, $Y_1$, $Y_2$, $R_3$, $R_4$, $R_6$, $R_7$, $R_8$, $R_9$, $R_{10}$, $R_{11}$, $R_{12}$ is deuterium or substituted with deuterium.

NSPs can include a compound according to Formula (V-b) or an optically pure stereoisomer, pharmaceutically acceptable salt, solvate, or prodrug thereof.

Formula (V-b)

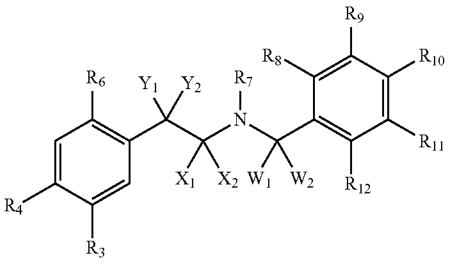

For some embodiments, $R_3$ and $R_6$ are —$OR^a$. For some embodiments, $R_4$ is selected from cyano, halogen, unsubstituted or substituted $C_1$-$C_6$ alkyl, —$OR^a$, and —$SR^a$.

For some embodiments, each $R^a$ is independently selected from hydrogen, deuterium, and unsubstituted or substituted $C_1$-$C_6$ alkyl.

For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl.

For some embodiments, $R_8$, $R_9$, and $R_{10}$ are independently selected from hydrogen and deuterium.

For some embodiments, $R_{11}$ and $R_{12}$ together with the atoms to which they are attached form an unsubstituted or substituted cycloalkyl, aryl, heterocycloalkyl, or heteroaryl.

For some embodiments, at least one of $W_1$, $W_2$, $X_1$, $X_2$, $Y_1$, $Y_2$, $R_3$, $R_4$, $R_6$, $R_7$, $R_8$, $R_9$, $R_{10}$, $R_{11}$, $R_{12}$ is deuterium or substituted with deuterium.

Psychedelic drugs can include a compound according to Formula (VI) or an optically pure stereoisomer, pharmaceutically acceptable salt, solvate, or prodrug thereof.

Formula (VI)

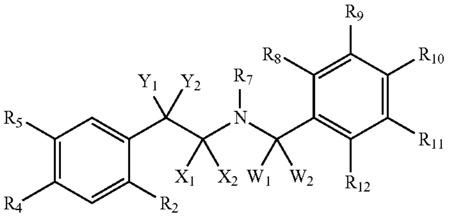

For some embodiments, $R_2$ and $R_5$ are —$OR^a$.

For some embodiments, $R_4$ is selected from hydrogen, deuterium, cyano, halogen, unsubstituted or substituted $C_1$-$C_6$ alkyl, —$OR^a$, and —$SR^a$.

For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl.

For some embodiments, $R_8$, $R_9$, and $R_{10}$ are independently selected from hydrogen, deuterium, hydroxyl, cyano, halogen, unsubstituted or substituted $C_1$-$C_6$ alkyl, —$OR^a$, and —$SR^a$.

For some embodiments, $R_{11}$ and $R_{12}$ are independently selected from hydrogen, deuterium, hydroxyl, cyano, halogen, unsubstituted or substituted $C_1$-$C_6$ alkyl, —$OR^a$, and —$SR^a$, or $R_{11}$ and $R_{12}$ together with the atoms to which they are attached form an unsubstituted or substituted cycloalkyl, aryl, heterocycloalkyl, or heteroaryl.

For some embodiments, each $R^a$ is independently selected from hydrogen, deuterium, and unsubstituted or substituted $C_1$-$C_6$ alkyl.

For some embodiments, at least one of $W_1$, $W_2$, $X_1$, $X_2$, $Y_1$, $Y_2$, $R_2$, $R_4$, $R_5$, $R_7$, $R_8$, $R_9$, $R_{10}$, $R_{11}$, $R_{12}$ is deuterium or substituted with deuterium.

Psychedelic drugs can include a compound according to Formula (VI-a) or an optically pure stereoisomer, pharmaceutically acceptable salt, solvate, or prodrug thereof.

Formula (VI-a)

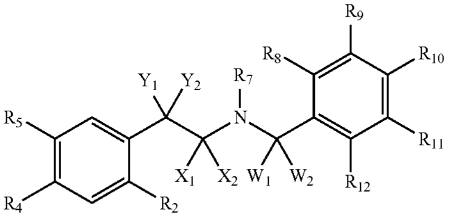

For some embodiments, $R_2$ and $R_5$ are —$OR^a$.

For some embodiments, $R_4$ is selected from cyano, halogen, unsubstituted or substituted $C_1$-$C_6$ alkyl, —$OR^a$, and —$SR^a$. For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl.

For some embodiments, $R_8$, $R_9$, $R_{10}$, and $R_{11}$ are independently selected from hydrogen and deuterium.

For some embodiments, $R_{12}$ is selected from hydroxyl, halogen, unsubstituted or substituted $C_1$-$C_6$ alkyl, —$OR^a$, and —$SR^a$.

For some embodiments, each $R^a$ is independently selected from hydrogen, deuterium, and unsubstituted or substituted $C_1$-$C_6$ alkyl.

For some embodiments, at least one of $W_1$, $W_2$, $X_1$, $X_2$, $Y_1$, $Y_2$, $R_2$, $R_4$, $R_5$, $R_7$, $R_8$, $R_9$, $R_{10}$, $R_{11}$, $R_{12}$ is deuterium or substituted with deuterium.

Psychedelic drugs can include a compound according to Formula (VI-b) or an optically pure stereoisomer, pharmaceutically acceptable salt, solvate, or prodrug thereof.

Formula (VI-b)

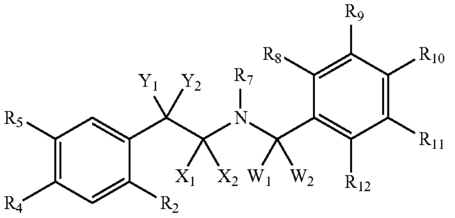

For some embodiments, $R_2$ and $R_5$ are —$OR^a$.

For some embodiments, $R_4$ is selected from cyano, halogen, unsubstituted or substituted $C_1$-$C_6$ alkyl, —$OR^a$, and —$SR^a$.

For some embodiments, $W_1$ and $W_2$ are independently selected from hydrogen, deuterium, and unsubstituted or substituted $C_1$-$C_6$ alkyl.

For some embodiments, $X_1$ and $X_2$ are independently selected from hydrogen, deuterium, and unsubstituted or substituted $C_1$-$C_6$ alkyl.

For some embodiments, $Y_1$ and $Y_2$ are independently selected from hydrogen, deuterium, and unsubstituted or substituted $C_1$-$C_6$ alkyl.

For some embodiments, $R_7$ is selected from hydrogen, deuterium, and unsubstituted or substituted $C_1$-$C_6$ alkyl.

For some embodiments, $R_8$, $R_9$, and $R_{10}$ are independently selected from hydrogen and deuterium.

For some embodiments, $R_{11}$ and $R_{12}$ together with the atoms to which they are attached form an unsubstituted or substituted cycloalkyl, aryl, heterocycloalkyl, or heteroaryl.

For some embodiments, each $R^a$ is independently selected from hydrogen, deuterium, and unsubstituted or substituted $C_1$-$C_6$ alkyl.

For some embodiments, at least one of $W_1$, $W_2$, $X_1$, $X_2$, $Y_1$, $Y_2$, $R_2$, $R_4$, $R_5$, $R_7$, $R_8$, $R_9$, $R_{10}$, $R_{11}$, $R_{12}$ is deuterium or substituted with deuterium.

For some embodiments, the compound is selected from the group consisting of

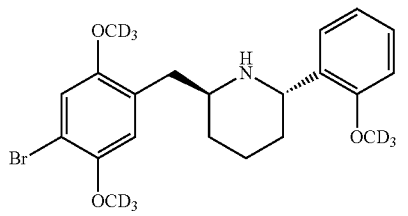

(S,S)-(-)-DMBMPP-Me-$d_9$ (Adelia-NSP1)
(2S,6S)-2-(4-bromo-2,5-bis(methoxy-$d_3$)benzyl)-6-(2-(methoxy-$d_3$)phenyl)piperidine

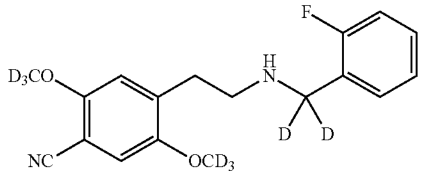

25CN-NBF-α,α-$d_2$-Me-$d_6$ (Adelia-NSP5)
4-(2-(((2-flourophenyl)methyl-$d_2$)amino)ethyl)-2,5-bis(methoxy-$d_3$)benzonitrile

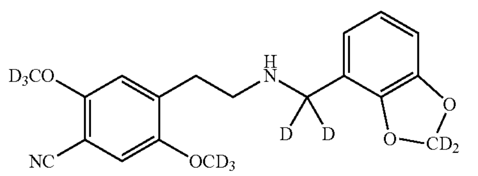

25CN-NBMD-α,α-$d_2$-Me-$d_6$-$CD_2$-$d_2$ (Adelia-NSP2):
4-(2-(((benzo[d][1,3]dioxol-4-yl-2,2-$d_2$)methyl-$d_2$)amino)ethyl)-2,5-bis(methoxy-$d_3$)benzonitrile

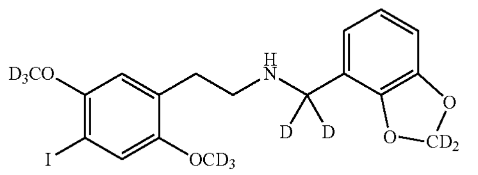

25I-NBMD-α,α-$d_2$-Me-$d_6$-$CD_2$-$d_2$ (Adelia-NSP6):
N-((benzo[d][1,3]dioxol-4-yl-2,2-$d_2$)methyl-$d_2$)-2-(4-iodo-2,5-bis(methoxy-$d_3$)phenyl)ethan-1-amine

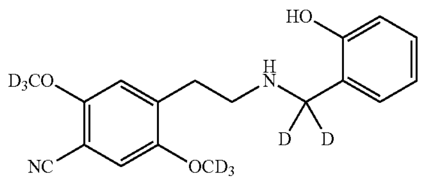

25CN-NBOH-α,α-$d_2$-Me-$d_6$ (Adelia-NSP3)
4-(2-(((2-hydroxyphenyl)methyl-$d_2$)amino)ethyl)-2,5-bis(methoxy-$d_3$)benzonitrile

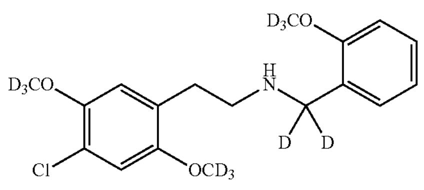

25C-NBOMe-α,α-$d_2$-Me-$d_9$ (Adelia-NSP7)
2-(4-chloro-2,5-bis(methoxy-$d_3$)phenyl)-N-((2-(methoxy-$d_3$)phenyl)methyl-$d_2$)ethan-1-amine -continued

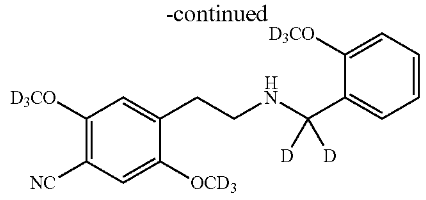

25CN-NBOMe-α,α-$d_2$-Me-$d_9$ (Adelia-NSP4)
2,5-bis(methoxy-$d_3$)-4-(2-(((2-(methoxy-$d_3$)phenyl)methyl-$d_2$)amino)ethyl)benzonitrile

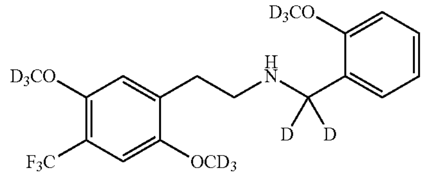

Cimbi-138* (4-$CF_3$)-α,α-$d_2$-Mc-$d_9$ (Adelia-NSP8)
2-(2,5-bis(methoxy-$d_3$)-4-(triflouromethyl)phenyl)-N-((2-(methoxy-$d_3$)phenyl)methyl-$d_2$)ethan-1-amine For some embodiments, the psychedelic drugs can include phenethylamine derivatives including, but not limited to, MDMA, MDEA, MBDB, TMA, DOM, DOET, DOI, DOC, tryptamine derivatives, including, but not limited to, DMT, 5-MeO-DMT, psilocybin, psilocin, compounds of Formula (I), Formula (II), Formula (II-a), Formula (II-b), Formula (II-c), Formula (II-d), Formula III, Formula (III-a), Formula (IV), Formula (IV-a), Formula (IV-b), Formula (V), Formula (V-a), Formula (V-b), Formula (VI), Formula (VI-a), Formula (VI-b), and any exemplary compounds described herein.

In some embodiments, a 5-HT2A receptor agonist and an NMDA receptor antagonist are combined in a pharmaceutical composition. It has been surprisingly found that the 5-HT2A receptor agonist and NMDA receptor antagonist (e.g., nitrous oxide) provide therapeutic efficacy while improving patient experience. For example, the 5-HT2A receptor agonist may be used in conjunction with the NMDA receptor antagonist (e.g., nitrous oxide) to reduce or eliminate psychological disorders such as acute psychedelic crisis (a bad trip), and dysphoric physiological and psychological side effects or other adverse events that can accompany psychedelic psychotherapy sessions.

Dosage of psychedelic drugs can vary. A pharmaceutical composition can include compositions wherein the psychedelic drug is contained in a therapeutically effective amount. An "effective amount" or a "therapeutically effective amount" is a sufficient amount of the drug to treat or ameliorate a condition, disorder, or disease. The actual amount effective for a particular application can depend, inter alia, on the condition being treated. The dosage and frequency (single or multiple doses) of psychedelic drug administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans can be determined (e.g., from animal models). For example, a dose for humans can be formulated to achieve a concentration that has been found to be effective in animals. The dosage in humans can be adjusted by monitoring response of the human to the treatment and adjusting the dosage upwards or downwards. Determination of the dosage and frequency of psychedelic drug administered is readily within the ability of one of ordinary skill in the medical field, taking into account the various factors noted above.

Dosages can be varied depending upon the requirements of the subject and the psychedelic drug being used. The dose administered to a subject, in the context of the psychedelic drugs presented herein, should be sufficient to affect a beneficial therapeutic response in the subject over time. The size of the dose also will be determined by the existence, nature, and extent of any adverse side effects. Treatment can be initiated with smaller dosages, which are less than the optimum dose of the psychedelic drug. Thereafter, the dosage can be increased by small increments until the optimum effect under the circumstances is reached.

Dosage amounts and intervals can be adjusted individually to provide levels of the administered compounds effective for the particular clinical indication being treated. This will provide a therapeutic regimen that is commensurate with the severity of the individual's disease state.

An effective prophylactic or therapeutic treatment regimen can be planned that does not cause substantial toxicity and yet is effective to treat the clinical symptoms demonstrated by the particular patient. This planning can involve the choice of psychedelic drug by considering factors such as compound potency, relative bioavailability, patient body weight, presence and severity of adverse side effects, mode of administration, and the toxicity profile of the selected psychedelic drug.

Psychedelic drugs can be administered via aerosol inhalation at about 1 μg to about 10.0 mg or more (or any range between about 1 μg to about 10.0 mg), e.g., about 1 μg, 2 μg, 5 μg, 6 μg, 10 μg, 13 μg, 15 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 300 μg, 400 μg, 500 μg, 1.0 mg, 2.0 mg, 3.0 mg, 4.0 mg, 5.0 mg, 6.0 mg, 7.0 mg, 8.0 mg, 9.0 mg, 10.0 mg or more per inhalation session. In an embodiment, a subject can have about 1, 2, 3, 4, 5 or more inhalation sessions a day. In an embodiment, a subject can have about 1, 2, 3, 4, 5 or more inhalation sessions every other day, twice a week, or three times a week. In an embodiment, a subject can have about 1, 2, 3, 4, 5 or more inhalation sessions every other month, twice a month, three times a month, or four times a month.

A pharmaceutical composition comprising a psychedelic drug can be prepared and administered in a wide variety of dosage formulations. Liquid form preparations include solutions and emulsions, wherein the solvent or carrier is, for example, water, water/propylene glycol solutions, or organic solvents.

Aqueous solutions suitable for inhalation use can be prepared by dissolving the active psychedelic drug or derivative thereof in water. Suitable stabilizers and thickening agents can also be added. Aqueous emulsions suitable for inhalation use can be made by dispersing the liquid psychedelic drug or derivative thereof in water with viscous material, such as natural or synthetic gums, resins, methylcellulose, sodium carboxymethylcellulose, and other suspending agents.

Some psychedelic drugs can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of an emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

In the salt form, psychedelic drugs or derivatives thereof can also be dissolved in organic solvents. Organic solvents can be, for example, acetonitrile, chlorobenzene, chloroform, cyclohexane, 1,2-dichloromethane, dichloromethane, 1,2-dimethoxyethane, N,N-dimethylacetamide, N,N-dimethylformamide, 1,4-dioxane, 20ethoxyethanol, ethylene glycol, formamide, hexane, methanol, 2-methoxyethanol, methybutylketone, methylcyclohexane, N-methylpyrrolidone, nitromethane, pyridine, sulfolane, tetralin, toluene, 1,1,2-trichloroethylene, or xylene. Organic solvents can belong to functional group categories such as ester solvents, ketone solvents, alcohol solvents, amide solvents, ether solvents, hydrocarbon solvents, etc. each of which can be used.

Aerosols

Devices used to deliver therapeutic agents as described herein as aerosols can be based on, for example, nebulizers, pressurized metered-dose inhaler (pMDI), and dry powder inhalers (DPIs). Pulmonary drug delivery is a form of drug targeting, whether to the site of action in the lungs for topically acting drugs, or the site of absorption for systemically acting drugs. For the former, the advantages of pulmonary delivery include the possibility to use a relatively low dose, a low incidence of systemic side effects and for some drugs a rapid onset of action. For systemically acting drugs, pulmonary delivery offers an opportunity to avoid oral administration and detrimental reactivity within the GI tract, or to avoid injections for drugs that are not well absorbed via the GI tract, along with the possibility for more advantageous pharmacokinetic profiles. The pulmonary epithelium, consisting of an area >100 $m^2$, and having an epithelial cell layer <1 μm in thickness, is an attractive target site for systemically acting drugs.

Delivering drugs by inhalation, however, can be relatively complex, for two main reasons. First, the respiratory tract has evolved defense mechanisms that are intended to keep inhaled materials out of the lungs, as well as removing or inactivating them once they have been deposited. Second, it is necessary for a patient to use an inhaler device, and to use it correctly. Failure to adhere to inhaled treatment regimens and misuse of delivery devices are common problems. These issues pose major challenges to the pharmaceutical industry and to healthcare professionals. The major problems with the use of inhalation to deliver drugs are the deposition of aerosolized particles in the oropharyngeal region and upper airways and the lack of coordination between the device activation and inhalation due to lack of patient training.

Devices for inhaled drug delivery have two basic functions, namely aerosol formation and facilitation of aerosol transport into the lungs. A distinction is made between passive and active devices. A passive device derives the energy required for aerosol formation from the inhaled air stream, i.e., from the patient, while active devices create the aerosol independently of the patient's inhalation. Inhalation devices can be further categorized in various ways, such as single-dose versus multi-dose, or disposable versus reusable. Multi-dose devices can provide benefits for chronic therapy, such as cost reduction, portability, and portability, ease of use and convenience. For irregular administrations and one-time applications, disposable devices may be more suitable. Furthermore, aspects such as the risk of device contamination acting as a reservoir for microbial growth and allowing the development of antibiotic resistance may affect the choice for a multi- or single-dose device.

Three main types of inhalation devices can be used for pulmonary delivery: pressurized metered dose inhalers (pMDIs), nebulizers, soft mist inhalers, and dry powder inhalers (DPIs). Each category of device has advantages and disadvantages.

In general, pMDIs generate aerosol faster than the patient can inhale. Coordination between device actuation and patient inhalation is especially difficult in children and the elderly. With some DPIs, it is required that the patient inhales at maximum force to disperse then inhale the powder, which unless properly trained, is rarely achieved. In these scenarios, most of the aerosol deposits in the upper airways. For pMDIs, this problem can be addressed by providing a spacer or by designing a breath-activated inhaler instead of breath-coordinated devices.

The effectiveness of pulmonary delivery is also dependent upon the breathing pattern of the patient. Rapid inspiration is not recommended when using pMDIs and nebulizers, since it creates a turbulent air flow and fast velocity which increases the deposition by impaction in the upper airways. However, rapid inspiratory air flow is required to deagglomerate drug particles for inhalation in DPI devices.

There are two main types of nebulizers, jet and ultrasonic, that differ in the force used to generate the aerosol from the respective liquid. Depending on the type, nebulizers can generate 1-5 μm droplets. Nebulizers do not require patient coordination between inhalation and actuation, thus they are useful for pediatric, elderly, ventilated, non-conscious patients, or those who are unable to use pMDIs or DPIs. Nebulizers have the capability of delivering larger doses compared to the other aerosol devices even though this will require longer administration times.

Nebulizer devices can be breath-enhanced, breath-actuated, and vibrating mesh nebulizers. The design of breath-enhanced jet nebulizers is modified to allow for air entrainment during inspiration and to vent the expired air outside of the device. The main advantage of this approach is to increase the output rate, which in turn will decrease the administration time.

Breath-actuated nebulizers emit aerosolized droplets only when the patient inhales. Therefore, no drug is wasted during exhalation as the case of regular jet nebulizers and dissemination of expensive or toxic drugs to the surrounding environment is avoided.

Vibrating mesh nebulizers have a mesh plate that, when it vibrates through the action of the piezoelectric element, breaks the liquid into very fine droplets, which increases the volume of aerosol deposited in the alveoli. Vibrating mesh nebulizers can have an electronic indicator that show when the patient is breathing appropriately and only then, it releases the dose, with droplet size of mass median aerodynamic diameter, 4 μm and minimum drug loss (~1%). Smart devices can include a vibrating mesh nebulizer coupled with an adaptive aerosol delivery software that adjusts the aerosol emission based on the breathing pattern of the patient, which reduces drug loss and increases the inhaled mass. Such a device can adjust the dose delivery based on patient's last three breaths and provide feedback after dose delivery.

Soft Mist Inhaler (SMI) inhalation devices can be used to deliver the compositions described herein. The SMI is a nebulizer, as it disperses a solution of the active agent into fine droplets. It differs from a traditional nebulizer in that it is a hand-held, portable device that does not require an external power source, but is actuated by a mechanical spring. The instantaneous formation of the aerosol is comparable to a pMDI; thus, proper actuation-inhalation coordination is necessary. While it generally takes longer before the entire aerosol is generated (1.5 s versus 0.21-0.36 s for an HFA-pMDI) and the aerosol is emitted as a slow-moving mist, this allows for a relatively high lung deposition.

In an embodiment, methods of delivering psychedelic drugs by aerosol inhalation are provided. An aerosol, such as a mist, can be delivered using air, oxygen, and/or oxygen and helium mixtures as a carrier gas. The air, oxygen, and/or oxygen and helium mixture can be delivered at room temperature or heated. In an embodiment, an aerosol, such as a mist comprising a psychedelic drug or derivative thereof is delivered via inhalation using heated helium-oxygen (heliox) mixtures. Due to very low viscosity of helium the helium-oxygen mixtures generate gaseous streams characterized by laminar flow that is a highly desirable feature for reaching out into the deep lung areas and reducing deposition of the drug in the respiratory tract, one of the major obstacles in dose delivery via inhalation. A patient can inhale a dissolved free-base or salt formulation of a psychedelic drug or a derivative thereof as a mist into an alveolar region of the patient's lungs. The psychedelic drug or derivative can be delivered to a fluid lining of the alveolar region of the lungs and can be systemically absorbed into patient blood circulation. Advantageously, these formulations can be effectively delivered to the blood stream upon inhalation to the alveolar regions of the lungs.

Devices suitable for delivery of heated or unheated air, oxygen, or helium-oxygen mixtures include, for example, continuous mode nebulizers Flo-Mist (Phillips) and Hope (B&B Medical Technologies) and the accessories such as regulators, e.g., Medipure™ Heliox-LCQ System (PraxAir) and control box, e.g., Precision Control Flow (PraxAir). In another embodiment, a full delivery setup can be a device as described in, for example, Russian patent RU199823U1.

The term "heliox" as used herein refers to breathing gas mixtures of helium gas (He) and oxygen gas ($O_2$). In some embodiments, the heliox mixture can contain helium in the mixture of helium and oxygen at about 50%, 60%, 70%, 80% or 90% and contain oxygen in the mixture of helium and oxygen at about 50%, 40%, 30%, 20%, or 10%. The heliox mixture can thus contain helium and oxygen in a 50:50, 60:40, 70:30, 80:20, 90:10 ratio. In some embodiments, heliox can generate less airway resistance through increased tendency to laminar flow and reduced resistance in turbulent flow.

The use of heat in heliox mixtures can further enhance drug delivery by increasing permeability of key physical barriers for drug absorption. Heating of mucosal surfaces can increase permeability by enhancing peripheral blood circulation and relaxing the interstitial junction, as well as other mechanisms. Helium has a thermal conductivity almost 10 times higher than oxygen and nitrogen and can facilitate heat transfer more efficiently. A dry heliox mixture can be used safely as a pretreatment step when warmed up to as high as 110° C. (e.g., heated to about 70, 80, 90, 100, or 110° C.), which can enable the dry heliox mixture to heat mucosal surfaces of the lung and respiratory tract more efficiently.

Various types of personal vaporizers can be used to deliver the therapeutic compositions described herein and are known in the art. In general, personal vaporizers are characterized by heating a solid drug or compound. Vaporizers can work by directly heating a solid drug or compound to a smoldering point. Vaporizing a solid or solid concentrate can be done by convection on conduction. Convection heating of solid concentrate involves a heating element coming into contact with water, or another liquid, which then vaporizes. The hot vapor in turn directly heats the solid or solid concentrate to a smoldering point, releasing a vapor to be inhaled by a user. Conduction heating involves direct contact between the solid or solid concentrate and the heating element, which brings the solid to a smoldering point, releasing vapor to be inhaled by a user. Though vaporizers present advantages over smoking in terms of lung damage, the drug/active agent that is vaporized can be substantially deteriorated by the vaporizing heat.

A vapor is a solid substance in the gas phase at a temperature lower than its critical temperature, meaning that the vapor can be condensed to a liquid by increasing the pressure on it without reducing the temperature.

An aerosol, as used herein, is a suspension of fine solid particles or liquid droplets in a gas phase (e.g., air, oxygen, helium, nitrous oxide, and other gases, as well as mixtures thereof). A mist, as used herein, is a subset of aerosols, differing from a vapor, and is a dispersion of liquid droplets (liquid phase) suspended in the gas phase (e.g., air, oxygen, helium, and mixtures thereof). The liquid droplets of a mist can comprise a psychedelic drug or derivative thereof dissolved in an aqueous liquid or organic solvent. The liquid phase of mist droplets can contain thousands or millions of molecules. The gas phase of a mist can comprise air, oxygen, helium, and mixtures thereof. Mists do not comprise solid particulates. Mists can be created by any suitable methods, including for example, use of an inhaler or nebulizer.

In an embodiment, psychedelic drugs are delivered via a nebulizer, which generates an aqueous-droplet aerosol, such as a mist, containing the psychedelic drugs, which is optionally combined with a heated helium-oxygen mixture. In an embodiment, the psychedelic drugs are delivered via a nebulizer, which generates an aqueous-droplet aerosol, such as a mist, containing the psychedelic drugs, which is combined with nitrous oxide or a nitrous oxide-air mixture. The nitrous oxide (being an NMDA receptor antagonist) can augment the effect of the psychedelic drug and provide the ability to use less psychedelic drug to obtain similar levels of effect.

For example, a preparation of a psychedelic drug can be placed into a liquid medium and put into an aerosol by a device, such as a nebulizer. In an embodiment, a nebulizer can be, for example, a pneumatic compressor nebulizer, an ultrasonic nebulizer, a vibrating mesh or horn nebulizer, or a microprocessor-controlled breath-actuated nebulizer. In another embodiment, a nebulizer device can be a device as described in, for example, Russian patent RU199823U1.

A nebulizer is a device that turns a drug, such as a psychedelic drug, in solution or suspension into a fine aerosol, such as a mist, for delivery to the lungs. A nebulizer can also be referred to as an atomizer. To atomize is to put a dissolved drug into an aerosol, such as a mist, form. To deliver a drug by nebulization, a drug can be dispersed in a liquid medium, for example, water, ethanol, or propylene glycol. Additionally, psychedelic drugs or derivatives there can be carried in a vehicle such as, for example liposomes, polymers, emulsions, micelles, nanoparticles, or polyethyleneimine (PEI). Liquid drug formations for nebulizers can be, for example, aqueous solutions or viscous solutions. After application of a dispersing forcer (e.g., jet of gas, ultrasonic waves, or vibration of mesh), the dissolved psychedelic drug is contained within liquid droplets, which are then inhaled. A mist can comprise liquid droplets containing the drug in air or another gaseous mixture (e.g., a mixture of helium and oxygen).

Jet nebulizers (also known as pneumatic nebulizers or compressor nebulizers) use compressed gas to make a mist. In an embodiment, a jet nebulizer is a microprocessor-controlled breath-actuated nebulizer, also called a breath-actuated nebulizer. A breath-actuated nebulizer creates a mist only when a patient is inhaling, rather than creating a mist continuously. A mist can be generated by, for example, passing air flow through a Venturi in a nebulizer bowl or cup. A Venturi is a system for speeding the flow of a fluid by constricting fluid in a cone shape tube. In the restriction, the fluid must increase its velocity, thereby reducing its pressure and producing a partial vacuum. As the fluid exits the constriction point, its pressure increases back to the ambient or pipe level pressure. This can form a low-pressure zone that pulls up droplets through a feed tube from a solution of drug in a nebulizer bowl, and in turn this creates a stream of atomized droplets, which flow to a mouthpiece. Higher air flows lead to a decrease in particle size and an increase in output. Due to droplets and solvent that saturates the outgoing gas, jet nebulizers can cool a drug solution in the nebulizer and increase solute concentration in the residual volume. A baffle in a nebulizer bowl or cup can be impacted by larger particles, retaining and returning them to the solution in the nebulizer bowl or cup to be reatomized. Entrainment of air through a nebulizer bowl as the subject inhales can increase mist output during inspiration. Generation of a mist can occur with a smaller particle size distribution, but using smaller particle sizes can result in an increased nebulization time.

The unit of measurement generally used for droplet size is mass median diameter (MMD), which is defined as the average droplet diameter by mass. This unit can also be referred to as the mass mean aerodynamic diameter, or MMAD. The MMD droplet size for jet nebulizers can be about 1.0, 1.5, 2.0, 2.5, 3.0, 3.5, 4.0, 5.0, 6.0, 7.0, 8.0, 9.0, 10.0 μm or more (or any range between about 1.0 and 10.0 μm), which can be smaller than that of ultrasonic nebulizers.

Ultrasonic nebulizers generate mists by using the vibration of a piezoelectric crystal, which converts alternating current to high-frequency (about 1 to about 3 MHz) acoustic energy. The solution breaks up into droplets at the surface, and the resulting mist is drawn out of the device by the patient's inhalation or pushed out by gas flow through the device generated by a small compressor. Ultrasonic nebulizers can include large-volume ultrasonic nebulizers and small-volume ultrasonic nebulizers. Droplet sizes tend to be larger with ultrasonic nebulizers than with jet nebulizers. The MMD droplet size for ultrasonic nebulizers can be about 2.0, 2.5, 3.0, 3.5, 4.0, 4.5, 5.0, 5.5, 6.0, 6.5, 7.0, 7.5, 8.0, 9.0, 10.0 μm or more (or any range between about 2.0 and 10.0 μm). Ultrasonic nebulizers can create a dense mist, with droplets at about 100, 150, 200, 250, 300 μm/L or more.

Mesh nebulizer devices use the vibration of a piezoelectric crystal to indirectly generate a mist. Mesh nebulizers include, for example, active mesh nebulizers and passive mesh nebulizers. Active mesh nebulizers use a piezo element that contracts and expands on application of an electric current and vibrates a precisely drilled mesh in contact with the drug solution to generate a mist. The vibration of a piezoelectric crystal can be used to vibrate a thin metal plate perforated by several thousand holes. One side of the plate is in contact with the liquid to be atomized, and the vibration forces this liquid through the holes, generating a mist of tiny droplets. Passive mesh nebulizers use a transducer horn that induces passive vibrations in the perforated plate with tapered holes to produce a mist. Examples of active mesh nebulizers include the Aeroneb® (Aerogen, Galway, Ireland) and the eFlow® (PARI, Starnberg, Germany), while the Microair NE-U22® (Omron, Bannockburn, IL) is a passive mesh nebulizer. Mesh nebulizers are precise and customizable. By altering the pore size of the mesh, the device can be tailored for use with drug solutions of different viscosities, and the output rate changed. Use of this method of atomization can offer several advantages. The size of the droplets can be extremely precise because droplet size can be determined by the size of the holes in the mesh (which may be tailor-made to suit the application). Nebulizer meshes can be manufactured using methods such as electrodeposition, electroplating, and laser cutting to produce a liquid particle in gas in the respirable range. Mesh can be made of metal alloy. The metals used in mesh manufacture can include platinum, palladium, nickel, and stainless steel. The size of the droplet is about twice the size of the mesh hole. Mesh holes, therefore, can be about 0.1, 0.5, 1.0, 1.5, 2.0, 2.5, 3.0, 3.5, 4.0, 4.5, 5.0 μm or more (or any value in between about 0.1 and 5.0 μm). Mist generation in mesh nebulizers can vary based on the shape of the mesh, the material that the mesh is made of, and the way that the mesh is created. In other words, different meshes can produce different sized liquid particles suspended in gas. Generally, MMD droplet size for mesh nebulizers can be about 1.0, 1.5, 2.0, 2.5, 3.0, 3.5, 4.0, 4.5, 5.0, 5.5, 6.0, 6.1, 6.2, 6.3, 6.4, 6.5, 6.6, 6.7, 6.8, 6.9, 7.0 μm or more (or any value in between about 1.0 and 7.0 μm).

Additionally, droplet size can be programmable. In particular, geometric changes can be made to a nebulizer to provide a specific desired droplet size. Additionally, droplet size can be controlled independently of droplet velocity. The volume of liquid atomized, and the droplet velocity can also be precisely controlled by adjusting the frequency and amplitude of the mesh vibration. Furthermore, the number of holes in the mesh and their layout on the mesh can be tailored. Mesh nebulizers can be powered either by electricity or by battery.

A mist output rate in standing cloud mL per minute (for any atomization methodology described herein) can range from, for example, 0.1, 0.2, 0.3, 0.4, 0.5, 0.6, 0.7, 0.8, 0.9 mL/minute or more (or any range between about 0.1 and 0.9 mL/minute) and the residual volume in any type of nebulizer reservoir can range from a about 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 mL or more (or any range between about 0.01 and 2.0 mL). Precise droplet size control can be advantageous since droplet size can correlate directly to kinetic drug release (KDR). Precise control of KDR can be achievable with precise control of droplet size. Psychedelic drugs or derivatives thereof can be delivered via a mist using any methodology with an MMD droplet size of about 0.5, 1.0, 1.5, 2.0, 2.5, 3.0, 3.5, 4.0, 5.0, 6.0, 7.0, 8.0, 9.0, 10.0 μm or more (or any range between about 0.5 and 10.0 μm).

In an embodiment, a psychedelic drug can be delivered via a continuous positive airway pressure (CPAP) or other pressure-assisted breathing device. A pressure-assisted breathing device forces a continuous column of compressed air or other gas at a fixed designated pressure against the face and nose of the patient, who is wearing a mask or nasal cap. When the patient's glottis opens to inhale, the pressure is transmitted throughout the airway, helping to open it. When the patient exhales, pressure from the deflating lungs and chest wall pushes air out against the continuous pressure, until the two pressures are equal. The air pressure in the airway at the end of exhalation is equal to the external air pressure of the machine, and this helps "splint" the airway open, allowing better oxygenation and airway recruitment. A pressure-assisted breathing device can be coupled with a means for introducing mist particles into the gas flow in the respiratory circuit and or a means for discontinuing the introduction of mist particles into the respiratory circuit when the patient exhales. See, e.g. U.S. Pat. No. 7,267,121.

In another embodiment, a mist can be delivered by a device such as a metered dose inhaler (MDI) (also referred to as a pressurized metered dose inhaler or pMDI), which generates an organic solvent-droplet mist containing the psychedelic drugs, which is optionally combined with a heated helium-oxygen mixture. In an embodiment, a psychedelic drug or derivative thereof can be delivered via a metered dose inhaler, MDI. MDI devices can include a canister which contains the psychedelic drug or derivative thereof and a propellant, a metering valve which dispenses the medicament from the canister, an actuator body that receives the canister and which forms an opening for oral inhalation, and an actuator stem which receives the drug from the canister and directs it out the opening in the actuator body. Moving the drug canister relative to the actuator body and actuator stem causes the metering valve to release the predetermined amount of the drug. In an embodiment, the psychedelic drug or derivative thereof can be dissolved in a liquid propellant mixture (sometimes including small amounts of a volatile organic solvent) stored in a pressurized container of the MDI. The "metered dose" is the dose that is prepackaged in a single-dose inhaler, or which in a multidose inhaler is automatically measured out of a reservoir in preparation for inhalation. MDI devices can be aided with spacers. An MDI spacer is a spacer that goes between the MDI and the mouth of a user of the MDI. An MDI spacer allows droplets in the atomized dose to settle out a bit and mix with air or other gas, thus allowing for more effective delivery of a metered dose into a user's lungs when inhaled. An MDI spacer assists in preventing a user from inhaling the metered dose directly from an MDI where the dose would be traveling so fast that the droplets of the atomized spray from the MDI hit and stick to the back of the user's throat rather than being inhaled into the user's lungs where the drug of the metered dose is designed to be delivered. MDI devices offer the advantage of regular dosing, which can be controlled in the manufacture of the drug.

Drugs can also be delivered by dry powder inhalers (DPI). In such DPI devices, the drug itself can form the powder or the powder can be formed from a pharmaceutically acceptable excipient or carrier and the drug is releasably bound to a surface of the carrier powder such that upon inhalation, the moisture in the lungs releases the drug from the surface to make the drug available for systemic absorption. In an embodiment, the psychedelic drug is delivered by use of a dry powder inhaler (DPI). Depending on the psychedelic drug used, the drug can be formed into the necessary powder itself, or can be releasably bound to a surface of a carrier powder. Such carrier powders are known in the art (see, e.g., H. Hamishehkar, et al., "The Role of Carrier in Dry Powder Inhaler", DOI: 10.5772/51209 (2012).).

DPI is generally formulated as a powder mixture of coarse carrier particles and micronized drug particles with aerodynamic particle diameters of 1-5 μm (Iida et al., "Preparation of dry powder inhalation by surface treatment of lactose carrier particles." Chem Pharm Bull, 511150009-2363 pubmed.ncbi.nlm.nih.gov/12520118/2003). Carrier particles are often used to improve drug particle flowability, thus improving dosing accuracy and minimizing the dose variability observed with drug formulations alone while making them easier to handle during manufacturing operations. Carrier particles should have several characteristics such as physico-chemical stability, biocompatibility and biodegradability, compatible with the drug substance and must be inert, available and economical. The choice of carrier particle (both content and size) is well within the purview of one of ordinary skill in the art. The most common carrier particles are made of lactose or other sugars, with α-lactose monohydrate being the most common lactose grade used in the inhalation field for such particulate carriers.

In an embodiment, any of the delivery devices above can be manufactured with smart technology enabling remote activation of the drug delivery. The remote activation can be performed via computer or mobile app. To ensure security, the remote activation device can be password encoded. This technology enables a healthcare provider to perform telehealth sessions with a patient, during which the healthcare provider can remotely activate and administer the psychedelic drug via the desired delivery device while supervising the patient on the televisit.

In an embodiment, the delivery device is an inhalation delivery device for delivery of a combination of nitrous oxide and a psychedelic drug by inhalation by a patient in need thereof, comprising an inhalation outlet portal for administration of the combination of nitrous oxide and the psychedelic drug to the patient; a container configured to deliver nitrous oxide gas to the inhalation outlet portal; and a device configured to generate and deliver an aerosol comprising the psychedelic drug to the inhalation outlet portal. In an embodiment, the inhalation outlet portal is selected from a mouthpiece or a mask covering the patient's nose and mouth. In an embodiment, the device configured to generate and deliver the aerosol to the inhalation outlet portal is a nebulizer. In an embodiment, the nebulizer is a jet nebulizer and the nitrous oxide gas acts as a driving gas for the jet nebulizer. In an embodiment, the device further comprises electronics configured to provide remote activation and operational control of the inhalation delivery device as noted above.

In an embodiment, the device is a dual delivery device configured to administer the psychedelic drug, such as in the form of an aerosol, and to simultaneously administer a controlled amount of nitrous oxide. Any of the above aerosol delivery devices can be used for such a device, with the addition of a source of nitrous oxide configured to provide a metered, controlled dose/flow rate of nitrous oxide through the same administration outlet as the aerosol delivery device. In an embodiment, the driving gas for the nebulization of the psychedelic drug is the nitrous oxide itself.

When co-administering the psychedelic drug with nitrous oxide, the nitrous oxide is can be in the form of a mixture of nitrous oxide and oxygen (or air), wherein the amount of nitrous oxide is 15 to 25% by volume of the nitrous oxide/oxygen (or air) mixture, e.g., about 15 to 20% by volume of the nitrous oxide/oxygen (or air) mixture.

Advantageously, low levels of nitrous oxide, at a level of about 15-25% by volume (e.g., about 25, 24, 23, 22, 21, 20, 19, 18, 17, 16, 15 or lower), for example about 15-20% by volume, for the about 90, 60, 45, 30, 15 minutes or less can provide good efficacy and with significantly reduced side effect profile. For example, the amount and/or severity of nausea, headache, anxiety, emotional discomfort, confusion, dizziness, and sedation can be reduced when low levels of nitrous oxide (e.g., a level of about 15-25%) is used. In a further embodiment, a mixture of nitrous oxide and oxygen (or air) is administered, without the administration of psychedelic drug. In such an embodiment, the mixture of nitrous oxide and oxygen (or air) contains the nitrous oxide in an amount of 15 to 25% by volume of the total gas, for example 15 to 20% by volume of the total gas. The time of administration of the nitrous oxide/oxygen (or air) mixture can be any desired duration, for example 20 to 60 mins or 30 to 45 mins.

In some additional embodiments, the co-administration of the psychedelic drug with nitrous oxide, in the form of a mixture of nitrous oxide and oxygen (or air), wherein the amount of nitrous oxide is about 15 to 25% by volume of the nitrous oxide/oxygen (or air) mixture, e.g., about 15 to 20% by volume of the nitrous oxide/oxygen (or air) mixture can reduce the amount of psychedelic drug to be delivered by about 2, 5, 10, 20, 30, 40, 50, 60, 70 percent or more (as compared to a dose not delivered with nitrous oxide as described herein. The lower amount of psychedelic drug can result in fewer or less severe side effects such as psychological disorders such as acute psychedelic crisis (a bad trip), dysphoric physiological and psychological side effects, nausea, headache, anxiety, emotional discomfort, confusion, dizziness, and sedation.

Delivery of Psychedelic Drugs and Helium Oxygen Mixtures

Methods disclosed herein provide for systemic delivery of small doses of a psychedelic drug or derivatives thereof. In particular, a psychedelic drug or derivatives thereof can be delivered to a patient's CNS. Doses can be optimized for individual patients' metabolisms and treatment needs. Larger doses with deleterious or undesirable side-effects can be avoided by using small doses. Methods of treating various central nervous system (CNS) diseases and other conditions are described herein. The methods can comprise delivering a psychedelic drug or derivative thereof to a patient in need thereof via inhalation of an aerosol comprising the drug and a gas such as air, oxygen, helium, or a mixture of helium and oxygen (i.e., a heliox mixture). In an embodiment the air, oxygen, helium, or mixture helium and oxygen can be heated. The method can further comprise a using a device containing a balloon with an oxygen-helium mixture equipped with a reducer and a mask connected to each other by a gas or air connecting tube, which contains an additional heating element capable of heating the gas mixture up to 120° C., a nebulizer with a vibrating porous plate or mesh, ensuring the passage of droplets with a size of less than 5 microns through it, and a disinfection unit.

In an embodiment a psychedelic drug or derivative thereof is delivered to the lower respiratory tract, for instance, to a pulmonary compartment such as alveoli, alveolar ducts and/or bronchioles. From there, the drug can enter the blood stream and travel to the central nervous system. In one embodiment of the present disclosure, delivering a psychedelic drug to a patient in need thereof via inhalation of a mist can deliver the psychedelic drug to the patient's CNS without passing through the liver. Administration via inhalation can allow gaseous drugs or those dispersed in a liquid or a mist, to rapidly deliver the psychedelic drug or derivative thereof to the blood stream, bypassing first-pass metabolism. First-pass metabolism, also known as "first-pass effect" or "presystemic metabolism" describes drugs that enter the liver and undergo extensive biotransformation.

In one embodiment of the present disclosure provides a treatment step, in which a psychedelic drug can be administered to a patient in need thereof by administering via inhalation a mixture of helium and oxygen heated to about 50° C., 51° C., 52° C., 53° C., 54° C., 55° C., 56° C., 57° C., 58° C., 59° C., 60° C., or more (or any range between 50° C. to 60° C.) and the atomized psychedelic drug or derivative thereof. In an embodiment a mist or vapor of the psychedelic drug can have a particle size from about 0.1 microns to about 10 microns (e.g., about 10, 5, 4, 3, 2, 1, 0.1 or less microns). In some embodiments, the psychedelic drug or derivative thereof can be atomized via a nebulizer creating an inhalant that is a mist with the dissolved psychedelic drug. In some embodiments, the atomized psychedelic drug is driven down the patient delivery line by the patient's inhalation. In another embodiment, the atomized psychedelic drug is driven down the patient delivery line by the patient's inhalation using a carrier gas. The carrier gas can be air, oxygen, a mix of oxygen and helium, heated air, heated oxygen, or heated helium and oxygen mixture.

In other embodiments of the present disclosure, the treatment step can be preceded by a pretreatment step. In some embodiments, the pretreatment step can comprise first administering a pretreatment inhalation therapy prior to administration of the mist of the psychedelic drug or derivative thereof. In some embodiments, the pretreatment inhalation step can comprise (i) administering via inhalation air, oxygen, or mixture of helium and oxygen heated to about 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., or more (or any range between about 90° C. and 120° C.) and no psychedelic drug, and then (ii) administering a treatment step of inhalation air, oxygen, a mix of oxygen and helium, heated air, heated oxygen, or heated helium and oxygen mixture. Heated air, heated oxygen, or heated helium and oxygen mixture, in combination with the atomized psychedelic drug or derivative thereof, can be heated to about 50° C., 51° C., 52° C., 53° C., 54° C., 55° C., 56° C., 57° C., 58° C., 59° C., 60° C., or more (or any range between about 50° C. and 60° C.).

In some embodiments of the present disclosure, step a pretreatment step (i) and a treatment step (ii) can be repeated 0, 1, 2, 3, 4, 5, or more times. In some embodiments of the present disclosure, steps (i) and (ii) can be repeated 0, 1, 2, 3, 4, 5, or more times followed by the treatment step, which can be repeated 0, 1, 2, 3, 4, 5, or more times. In some embodiments of the present disclosure, the treatment step can be repeated 0, 1, 2, 3, 4, 5, or more times with no pretreatment step.

Treatment, with optional pretreatment, can be administered once a week, twice a week, once a day, twice a day, three times a day or more. Each treatment can be for about 1, 5, 10, 20, 30, 45, 60 or more minutes.

A drug delivery procedure can comprise an inhaled priming no-drug hot heliox mixture to effectively preheat the mucosal bed followed by inhaling an atomized psychedelic drug, again driven by the heated heliox, but at lower temperatures, that are now dictated by lower heat tolerance to the wet vs. dry inhaled gas stream. Consequently, this procedure can be conducted in multiple repeated cycles, wherein a target PK and drug exposure is controlled by the concentration of the drug, temperature, flow rate of the helium oxygen mixture, composition of the mixture, number and durations of cycles, time and combinations of the above.

Methods of delivery described herein can be used to treat certain diseases and disorders. Treating and treatment refers to methods of alleviating or abrogating a condition, disorder, disease, one or more symptoms of a condition, disorder, or disease, or combinations thereof. Treating or treatment can include partial or complete halting of the progression of the condition, disorder, disease, or partial or complete reversal of the condition, disorder, disease. A treatment can provide a therapeutic benefit such as the eradication or amelioration of one or more of the physiological or psychological symptoms associated with the underlying condition, disease, or disorder such that an improvement is observed in the patient, notwithstanding the fact that the patient may still be affected by the condition.

Therefore, provided herein are methods of treating a central nervous system (CNS) disorder or psychological disorder comprising administering via inhalation a heated mixture of helium and oxygen heated and an atomized psychedelic drug. The treatment can alleviate one or more symptoms of the disorder.

In some embodiments, the psychedelic drug can be administered for treatment of CNS disease or other disorder. In some embodiments, the psychedelic drug can be administered to treat depression including, but not limited to major depression, melancholic depression, atypical depression, or dysthymia. In some embodiments the psychedelic drug can be administered to treat psychological disorders including anxiety disorder, obsessive compulsive disorder, addiction (narcotic addiction, tobacco addiction, opioid addiction), alcoholism, depression and anxiety (chronic or related to diagnosis of a life-threatening or terminal illness), compulsive behavior, or a related symptom.

In some embodiments, the disease or disorder can include central nervous system (CNS) disorders and/or psychological disorders, including, for example, post-traumatic stress disorder (PTSD), major depressive disorder (MDD), treatment-resistant depression (TRD), suicidal ideation and suicide attempts, bipolar and related disorders (including but not limited to bipolar I disorder, bipolar II disorder, cyclothymic disorder), obsessive-compulsive disorder (OCD), generalized anxiety disorder (GAD), acute psychedelic crisis, social anxiety disorder, substance use disorders (including but not limited to alcohol use disorder, opioid use disorder, amphetamine use disorder, nicotine use disorder, and cocaine use disorder), Alzheimer's disease, cluster headache and migraine, attention deficit hyperactivity disorder (ADHD), pain and neuropathic pain, aphantasia, childhood-onset fluency disorder, major neurocognitive disorder, mild neurocognitive disorder, gambling disorder, eating disorders such as anorexia nervosa, bulimia nervosa, binge-eating disorder, etc., and paraphilic disorders such as, for example, pedophilic disorder, exhibitionistic disorder, voyeuristic disorder, fetishistic disorder, sexual masochism or sadism disorder, and transvestic disorder, etc., sexual dysfunction, and obesity. In some embodiments, the disease or disorder may include conditions of the autonomic nervous system (ANS). In some embodiments, the disease or disorder may include pulmonary disorders (e.g., asthma and chronic obstructive pulmonary disorder (COPD). In some embodiments, the disease or disorder may include cardiovascular disorders (e.g., atherosclerosis).

The methods of delivering a psychedelic drug to the CNS (systemic drug delivery) via inhalation, such as through a nebulizer or other device as described herein (including, for example, using a heated helium-oxygen mixture), can lead to advantageous improvements in multiple PK parameters as compared to oral delivery. In particular, a psychedelic drug can cross the blood brain barrier and be delivered to the brain. As compared to oral delivery, the method of delivering a psychedelic drug to the CNS via inhalation, such as with a nebulizer or other device as described herein, optionally with a heated heliox mixture, can increase bioavailability by at least 25% as compared to oral delivery. In some embodiments, the method of delivering a psychedelic drug to the CNS via inhalation, such as with a nebulizer or other device as described herein, can increase bioavailability by about 10%, 25%, 30%, 35%, 40%, 50%, 55%, 60%, 65%, 70%, 80%, 85%, 90%, 95%, 99%, 99.9%, or more. The method of delivering a psychedelic drug to the CNS via nebulizer as described herein, can reduce $T_{max}$ by at least 50% as compared to oral delivery. In some embodiments, the method of delivering a psychedelic drug to the CNS via nebulizer as described herein, can reduce $T_{max}$ by at 30%, 40%, 50%, 55%, 60%, 65%, 70%, 80%, 85%, 90%, 95%, 99%, 99.9%, or more. In some embodiments, the method of delivering a psychedelic drug to the CNS via nebulizer or other device as described herein, can increase $C_{max}$ by at least 25% as compared to oral delivery. In some embodiments, the method of delivering a psychedelic drug to the CNS via nebulizer or other device as described herein, can increase $C_{max}$ by about 10%, 25%, 30%, 35%, 40%, 50%, 55%, 60%, 65%, 70%, 80%, 85%, 90%, 95%, 99%, 99.9%, or more. Furthermore, a method of delivering a psychedelic drug to the CNS via inhalation via a nebulizer or other device as described herein, can allow clinical protocols enabling dose titration and more controlled exposure. Controlled exposure enables adjusting the patient experience and providing overall improved therapeutic outcomes. With the smart technology enabled devices for inhalation delivery noted above, the dose titration and controlled delivery can be performed remotely by the healthcare worker, enabling the patient to be in the comfort of their own home, improving the patient's experience and outcome.

In an embodiment, a system is provided for administering psychedelic drugs (or salts thereof) that includes a container comprising a solution of a psychedelic drug (or derivative or salt thereof) compound formulation and a nebulizer physically coupled or co-packaged with the container and adapted to produce an aerosol, such as a mist, of the solution having a particle size from about 0.1 microns to about 10 microns (e.g., about 10, 5, 4, 3, 2, 1, 0.1 or less microns).

A patient or subject can be any mammal including, for example, a human. A patient or subject can have a condition to be treated or can be susceptible to a condition to be treated.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Example 1 Inhalation Delivery of DMT by Nebulization

DMT hydrochloride was formulated for nebulization by dissolving in water (buffered to pH 7 by isotonic phosphate buffer) to a concentration of 5 mg/ml. The freshly prepared solution (5 ml) was loaded into the Aerogen Solo (Aerogen Corp., Dangan, Ireland) mesh nebulizer with a palladium mesh and connected to a continuous nebulization tube set. The rate of delivery of the solution to the nebulizer compartment was set to 0.2-1 ml/min to enable a therapeutic dose delivery by titration. The nebulized aerosol was delivered to a patient via a face mask for a period of 5-20 min. For the first administration, the procedure was terminated as soon as patients achieved the onset of psychedelic effects which was determined by the patient's reporting and EEG live readouts.

Example 2 Inhalation Delivery of DMT by Metered-Dose Inhaler

DMT free base was dissolved in HFA propellant 227 (20 mg/ml) and loaded in the pressurized stainless steel cannister (V=14 ml) of the metered dose inhaler equipped with a Bespak's BK357 valve and actuator (orifice d=0.22 mm) by Recipharm chosen to deliver 0.1 ml as a standard drug dose. In order to achieve dose titration, the patients were administered up to 10 drug doses every 2 min over a period of 20 min. For the first administration, the procedure was terminated as soon as patients achieved the onset of psychedelic effects which was determined by the patient's reporting and EEG live readouts.

Obviously, numerous modifications and variations of the disclosed methods and compositions are possible in light of the above teachings. It is therefore to be understood that within the scope of the appended claims, the compositions and methods may be practiced otherwise than as specifically described herein.

The invention claimed is:

1. A method of delivering a psychedelic drug to a patient in need thereof, comprising:

administering an aerosol to the patient by inhalation, wherein the aerosol comprises the psychedelic drug in a carrier, and the psychedelic drug is a compound of Formula (II) or a stereoisomer, pharmaceutically acceptable salt, solvate, or prodrug thereof Formula (II)

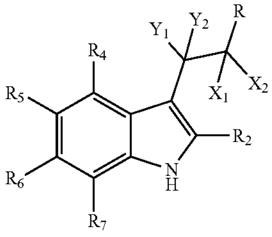

wherein:

$X_1$ and $X_2$ are deuterium, $Y_1$ and $Y_2$ are independently selected from hydrogen and deuterium, R is

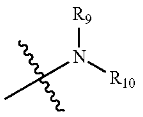

or

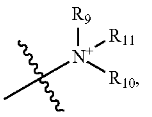

$R_2$ is selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, $R_4$ is selected from hydrogen, deuterium, unsubstituted or substituted alkoxy, and unsubstituted or substituted phosphoryloxy, $R_5$ is selected from hydrogen, deuterium, hydroxyl, and unsubstituted or substituted phosphoryloxy, $R_6$ and $R_7$ are selected from hydrogen, deuterium, and halogen, and $R_9$, $R_{10}$, and $R_{11}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

2. The method of claim 1, wherein the carrier is air, oxygen, or a mixture of helium and oxygen.

3. The method of claim 2, wherein the carrier is the mixture of helium and oxygen optionally heated to about 50° C. to about 60° C.

4. The method of claim 3, wherein the helium is present in the mixture of helium and oxygen at about 50% to 90% and the oxygen is present in the mixture of helium and oxygen at about 10% to 50%.

5. The method of claim 1, further comprising administering a pretreatment inhalation therapy prior to administration of the aerosol comprising the psychedelic drug and the carrier, wherein the pretreatment inhalation therapy comprises administering via inhalation a mixture of helium and oxygen heated to about 90° C. to about 120° C. to the patient.

6. The method of claim 1, wherein the aerosol is a mist.

7. The method of claim 1, wherein the aerosol is prepared by nebulization of the psychedelic drug using a member selected from the group consisting of a jet nebulizer, an ultrasonic nebulizer, a breath-actuated nebulizer, and a vibrating mesh nebulizer.

8. The method of claim 7, wherein the nebulization is performed using a driving gas comprising nitrous oxide for entrainment of the nebulized psychedelic drug.

9. The method of claim 8, wherein the nitrous oxide is present in the driving gas at a concentration of 15 to 25% by volume.

10. A method of treating a central nervous system (CNS) disorder or psychological disorder in a patient, comprising:

administering to the patient, via inhalation, an aerosol comprising a psychedelic drug in a carrier, wherein the psychedelic drug is a compound of Formula (II) or a stereoisomer, pharmaceutically acceptable salt, solvate, or prodrug thereof Formula (II)

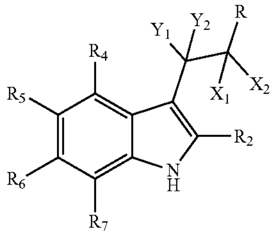

wherein:

$X_1$ and $X_2$ are deuterium, $Y_1$ and $Y_2$ are independently selected from hydrogen and deuterium, R is

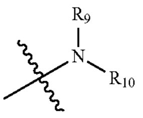

or

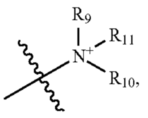

$R_2$ is selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, $R_4$ is selected from hydrogen, deuterium, unsubstituted or substituted alkoxy, and unsubstituted or substituted phosphoryloxy, $R_5$ is selected from hydrogen, deuterium, hydroxyl, and unsubstituted or substituted phosphoryloxy, $R_6$ and $R_7$ are selected from hydrogen, deuterium, and halogen, and $R_9$, $R_{10}$, and $R_{11}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl;

wherein the CNS disorder or psychological disorder is at least one selected from the group consisting of melancholic depression, atypical depression, dysthymia, anxiety disorder, obsessive compulsive disorder, addiction disorder, opioid use disorder, amphetamine use disorder, nicotine use disorder, cocaine use disorder, post-traumatic stress disorder (PTSD), major depressive disorder (MDD), treatment-resistant depression (TRD), suicidal ideation and suicide attempts, bipolar I disorder, bipolar II disorder, cyclothymic disorder, obsessive-compulsive disorder (OCD), generalized anxiety disorder (GAD), social anxiety disorder, Alzheimer's disease, cluster headache, migraine headaches, attention deficit hyperactivity disorder (ADHD), pain and neuropathic pain, aphantasia, childhood-onset fluency disorder, major neurocognitive disorder, mild neurocognitive disorder, sexual dysfunction, gambling disorder, eating disorder, anorexia nervosa, bulimia nervosa, binge-eating disorder, paraphilic disorders, pedophilic disorder, exhibitionistic disorder, voyeuristic disorder, fetishistic disorder, sexual masochism disorder, sexual sadism disorder, and transvestic disorder.

11. The method of claim 10, wherein the aerosol is a mist.

12. The method of claim 10, wherein the carrier is air, oxygen, or a mixture of helium and oxygen.

13. The method of claim 12, wherein the carrier is the mixture of helium and oxygen and the mixture of helium and oxygen is heated to about 50° C. to about 60° C. prior to administering the aerosol to the patient.

14. The method of claim 10, wherein the CNS disorder or psychological disorder is at least one selected from the group consisting of melancholic depression, atypical depression, dysthymia, anxiety disorder, major depressive disorder (MDD), treatment-resistant depression (TRD), suicidal ideation and suicide attempts, generalized anxiety disorder (GAD), and social anxiety disorder.

15. The method of claim 10, wherein the aerosol is prepared by nebulization of the psychedelic drug using a member selected from the group consisting of a jet nebulizer, an ultrasonic nebulizer, a breath-actuated nebulizer, and a vibrating mesh nebulizer.

16. The method of claim 15, wherein the nebulization is performed using a driving gas comprising nitrous oxide for entrainment of the nebulized psychedelic drug.

17. The method of claim 16, wherein the nitrous oxide is present in the driving gas at a concentration of 15 to 25% by volume.

18. A method of delivering a psychedelic drug to a patient in need thereof, comprising:

administering a dry powder to the patient by inhalation via a dry powder inhaler, wherein the dry powder comprises the psychedelic drug, and the psychedelic drug is a compound of Formula (II) or a stereoisomer, pharmaceutically acceptable salt, solvate, or prodrug thereof Formula (II)

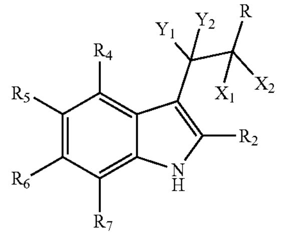

wherein:

$X_1$ and $X_2$ are deuterium, $Y_1$ and $Y_2$ are independently selected from hydrogen and deuterium, R is

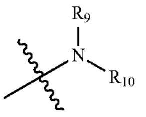

or

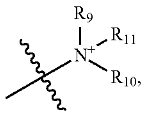

$R_2$ is selected from hydrogen, deuterium, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, $R_4$ is selected from hydrogen, deuterium, unsubstituted or substituted alkoxy, and unsubstituted or substituted phosphoryloxy, $R_5$ is selected from hydrogen, deuterium, hydroxyl, and unsubstituted or substituted phosphoryloxy, $R_6$ and $R_7$ are selected from hydrogen, deuterium, and halogen, and $R_9$, $R_{10}$, and $R_{11}$ are independently selected from hydrogen, unsubstituted or substituted alkyl, unsubstituted or substituted allyl, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

19. The method of claim 18, wherein the dry powder comprises a particulate carrier having the psychedelic drug on a surface thereof.

20. The method of claim 18, wherein the dry powder is formed of the psychedelic drug in solid particulate form.

* * * * *